United States Patent
Coburn et al.

(10) Patent No.: US 9,034,929 B2
(45) Date of Patent: *May 19, 2015

(54) AMINOALCOHOL AND BIOCIDE COMPOSITIONS FOR AQUEOUS BASED SYSTEMS

(75) Inventors: Charles E. Coburn, Vernon Hills, IL (US); John L. Pohlman, Skokie, IL (US); Bonnie A. Pyzowski, Park Ridge, IL (US); Patrick E. Brutto, Bloomingdale, IL (US); George David Green, Cary, IL (US); Raymond J. Swedo, Mt. Prospect, IL (US)

(73) Assignee: ANGUS Chemical Company, Buffalo Grove, IL (US)

( * ) Notice: Subject to any disclaimer, the term of this patent is extended or adjusted under 35 U.S.C. 154(b) by 357 days.

This patent is subject to a terminal disclaimer.

(21) Appl. No.: 12/521,825

(22) PCT Filed: Dec. 13, 2007

(86) PCT No.: PCT/US2007/087365

§ 371 (c)(1),
(2), (4) Date: Jun. 30, 2009

(87) PCT Pub. No.: WO2008/088632

PCT Pub. Date: Jul. 24, 2008

(65) Prior Publication Data

US 2010/0093736 A1     Apr. 15, 2010

Related U.S. Application Data

(60) Provisional application No. 60/880,333, filed on Jan. 12, 2007, provisional application No. 60/899,450, filed on Feb. 5, 2007.

(51) Int. Cl.
| | |
|---|---|
| C07C 211/00 | (2006.01) |
| C09K 8/524 | (2006.01) |
| A01N 33/18 | (2006.01) |
| A01N 33/24 | (2006.01) |
| A61K 31/045 | (2006.01) |
| C09D 5/14 | (2006.01) |
| A01N 33/08 | (2006.01) |
| A01N 43/80 | (2006.01) |
| C07C 215/08 | (2006.01) |
| C10M 141/06 | (2006.01) |
| C10M 141/08 | (2006.01) |

(52) U.S. Cl.
CPC *C09D 5/14* (2013.01); *A01N 33/08* (2013.01); *A01N 43/80* (2013.01); *C07C 215/08* (2013.01); *C10M 141/06* (2013.01); *C10M 141/08* (2013.01); *C10M 2203/106* (2013.01); *C10M 2207/023* (2013.01); *C10M 2207/046* (2013.01); *C10M 2207/08* (2013.01); *C10M 2207/127* (2013.01); *C10M 2207/18* (2013.01); *C10M 2207/281* (2013.01); *C10M 2211/042* (2013.01); *C10M 2215/042* (2013.01); *C10M 2215/044* (2013.01); *C10M 2215/10* (2013.01); *C10M 2215/102* (2013.01); *C10M 2215/16* (2013.01); *C10M 2215/202* (2013.01); *C10M 2215/222* (2013.01); *C10M 2215/226* (2013.01); *C10M 2219/044* (2013.01); *C10M 2219/066* (2013.01); *C10M 2219/09* (2013.01); *C10M 2219/104* (2013.01); *C10M 2223/04* (2013.01); *C10N 2230/16* (2013.01)

(58) Field of Classification Search
None
See application file for complete search history.

(56) References Cited

U.S. PATENT DOCUMENTS

| | | | |
|---|---|---|---|
| 2,164,271 A | 6/1939 | Hass et al. | |
| 2,695,222 A | 11/1954 | Chenicek et al. | |
| 3,247,054 A | 4/1966 | Hodge et al. | |
| 4,074,013 A | 2/1978 | Koch et al. | |
| 4,166,725 A | 9/1979 | Amick | |
| 4,708,720 A | 11/1987 | Grangette et al. | |
| 4,877,552 A | 10/1989 | Haring | |
| 4,925,582 A | 5/1990 | Bennett | |
| 5,154,817 A | 10/1992 | Reid | |
| 5,454,983 A | 10/1995 | Michael et al. | |

(Continued)

FOREIGN PATENT DOCUMENTS

| | | |
|---|---|---|
| JP | 52-025705 | 2/1977 |
| JP | 08193015 | 7/1996 |

(Continued)

OTHER PUBLICATIONS

Mulla et al. "Intramolecular Hydrogen Bonding and Intermolecular Association of Amino Alcohols", J.Chem.Soc.FaradayTrans.1, 1986, vol. 82, pp. 691-706.*

Freedman, "Intramolecular H-Bonds: A Spectroscopic Study of the Hydrogen Bond between Hydroxyl and Nitrogen", JACS, 1961, vol. 83, pp. 2900-2905.*

Hornhardt et al. "Static and Dynamic Dielectric Properties of Aminoalcohols in their Pure Liquid State and in Mixtures with Dioxane", J.Mol.Liq., 1996, vol. 69, pp. 201-209.*

(Continued)

*Primary Examiner* — Jeffrey S Lundgren
*Assistant Examiner* — Stephanie Springer
(74) *Attorney, Agent, or Firm* — Foley & Lardner LLP

(57) ABSTRACT

Biocidal compositions and their use in aqueous media, such as metalworking fluids, the compositions comprising a biocidal agent; and a non-biocidal primary amino alcohol compound of the formula (I); wherein $R^1$, $R^2$, $R^3$, $R^4$, and $R^5$ are as defined herein.

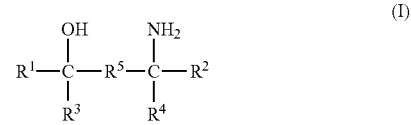

(I)

18 Claims, 17 Drawing Sheets

(56) References Cited

U.S. PATENT DOCUMENTS

| | | |
|---|---|---|
| 5,854,268 A | 12/1998 | Baker et al. |
| 6,267,791 B1 | 7/2001 | Thomas et al. |
| 6,607,566 B1 | 8/2003 | Coleman et al. |
| 2003/0027889 A1 | 2/2003 | Inhester et al. |
| 2003/0162845 A1 | 8/2003 | O'Reilly et al. |
| 2003/0209165 A1 | 11/2003 | Gernon |
| 2005/0266235 A1 | 12/2005 | Nakajima et al. |

FOREIGN PATENT DOCUMENTS

| | | |
|---|---|---|
| WO | 91/17746 A1 | 11/1991 |
| WO | 94/12028 A1 | 6/1994 |
| WO | 2004/057964 A1 | 7/2004 |
| WO | 2006016991 | 2/2006 |
| WO | 2007018782 | 2/2007 |
| WO | 2007032918 | 3/2007 |
| WO | 2008088632 | 7/2008 |
| WO | 2009140062 | 11/2009 |

OTHER PUBLICATIONS

Altenhoff, et al., Sterically Demanding, Bioxazoline-Derived N-Heterocyclic Carbene Ligands with Restricted Flexibility for Catalysis, J. Am. Chem. Soc. 2004, 126, 15195-1520; supplemental information.

U.S. Office Action dated Jun. 27, 2013 from U.S. Appl. No. 12/988,404.

Noland, et al., Derivatives of (1-Aminocyclohexyl)methanol, Jun. 1957, p. 695-697.

Database WPI Week 199640, Thomson Scientific, London GB; AN 1996-397196 XP002509608 & JP 08193015 abstract.

Macleod et al., "Cation Antagonism of the Antibacterial Action of Amines", Inorganic Ions and Amine Toxicity, 1951, pp. 193-201.

Kubis et al., "Investigation on Antibacterial Action of Some Amines", Pharmazie, 1983, pp. 488-489, vol. 38, H. 7.

Sandin et al., "The role of alkyl chain length on the antibacterial activity of alkyl ethanolamines", Biomedical Letters, 1992, pp. 85-92, vol. 47, The Faculty Press.

Borrows et al., "Preparation and Properties, etc: Preparation and Properties of Some Long-Chain Aliphatic Amines", 1947, pp. 197-202, Chapter 47.

Gernon, "Arkema and Metalworking", Arkema Inc., Tribology & Lubrication Technology 2005, pp. 38-40, vol. 61 No. 11.

Brutto et al., "Some Key Building Blocks for Long-Life Bioresistant Metalworking Fluids", Powerpoint Presentation at STLE Annual Meeting, 2005.

"An Outstanding Multi-functional Amine Additive for Metalworking Fluids", Synergex Premier.

Aitken et al., "Studies on the Condensation Products from N-Primary 1,2-Amino Alcohols and Formaldehyde", Heterocycles, 2004, vol. 64, pp. 277-289.

Robbins et al., "A review of the microbiological degradation of fuel", Directory of Microbiocides for the Protection of Materials: A Handbook, 2005, pp. 177-202.

Database WPI Week 199640 Thomson Scientific, London, GB AN 1996-397196 XP002516784.

"Metalworking Fluid Additives." ANGUS Chemical Company.

Notice of Reasons for Rejection on Japanese Application 2014-002600, mailed Dec. 16, 2014.

* cited by examiner

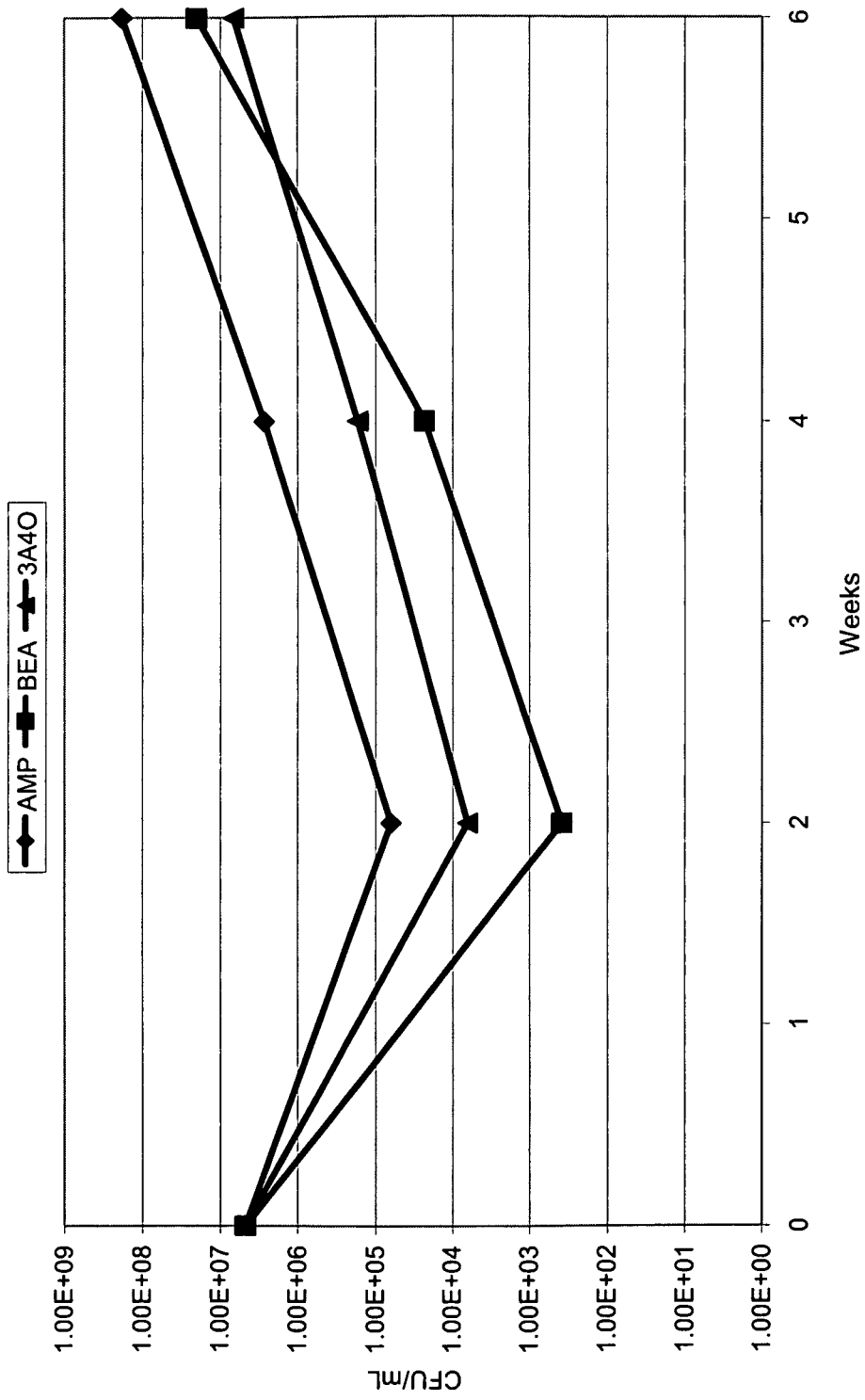
Figure 1 - Fluids Without Preservative - Bacterial Data

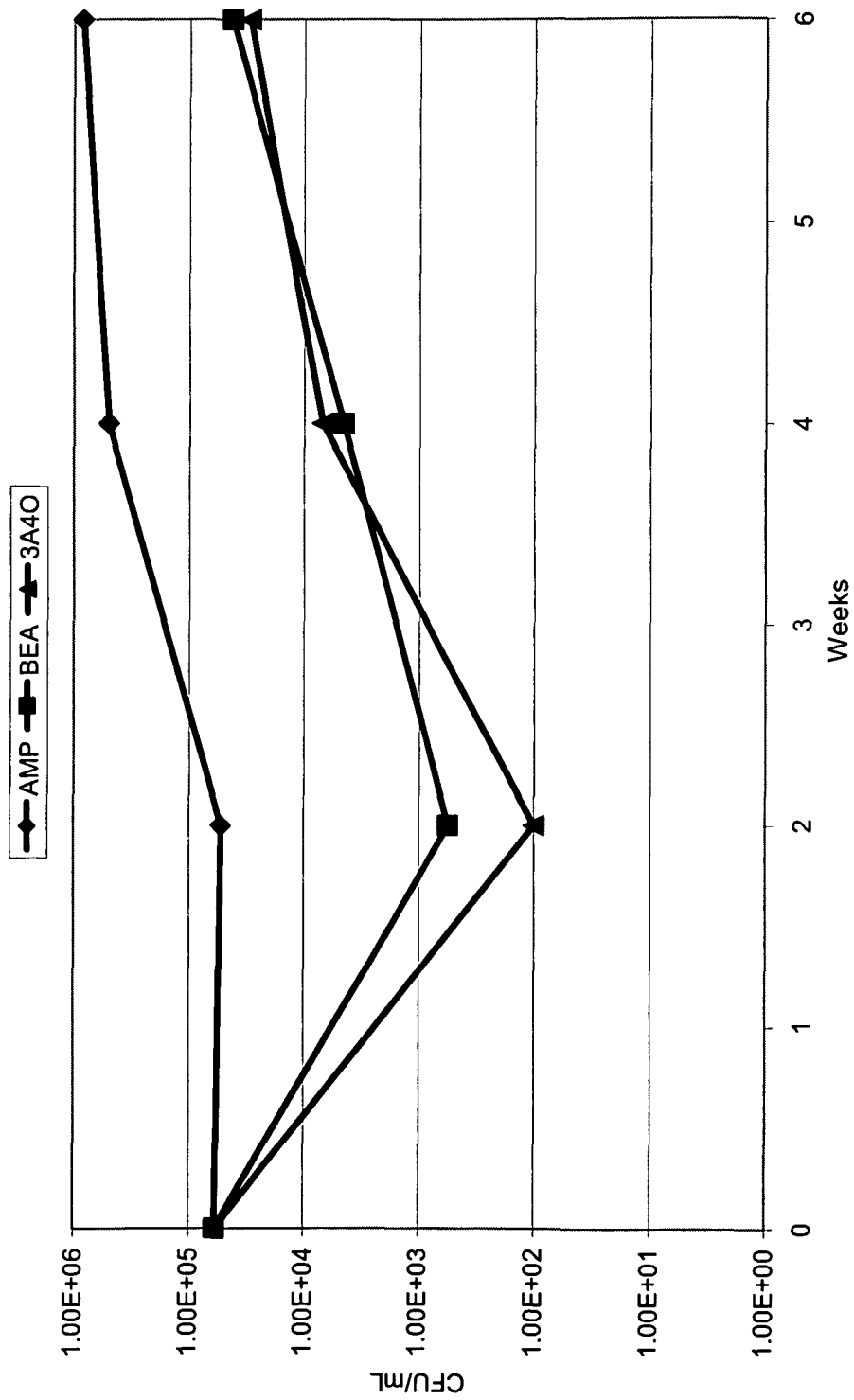

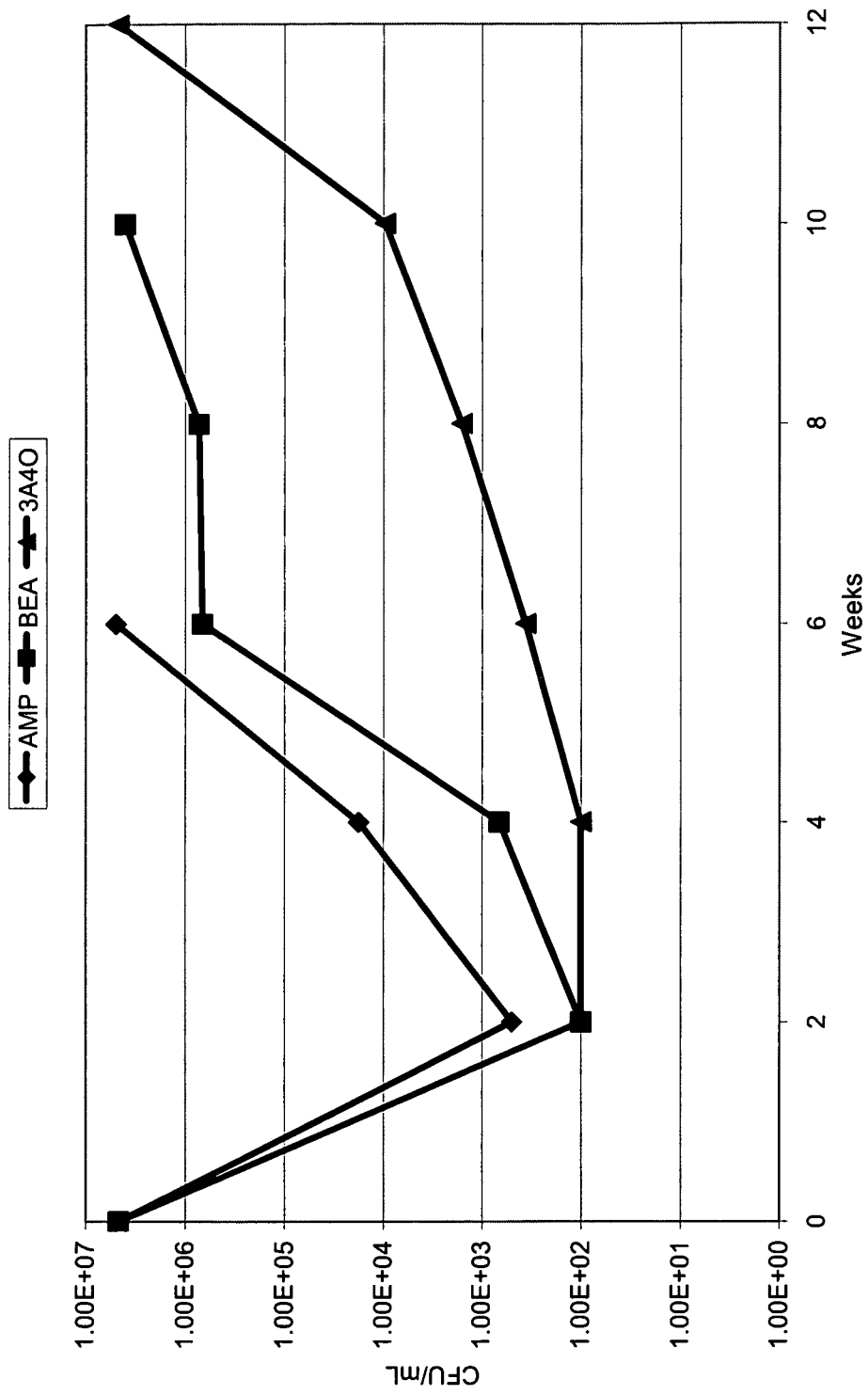
Figure 3 - Fluids Preserved with Triazine - Bacterial Data

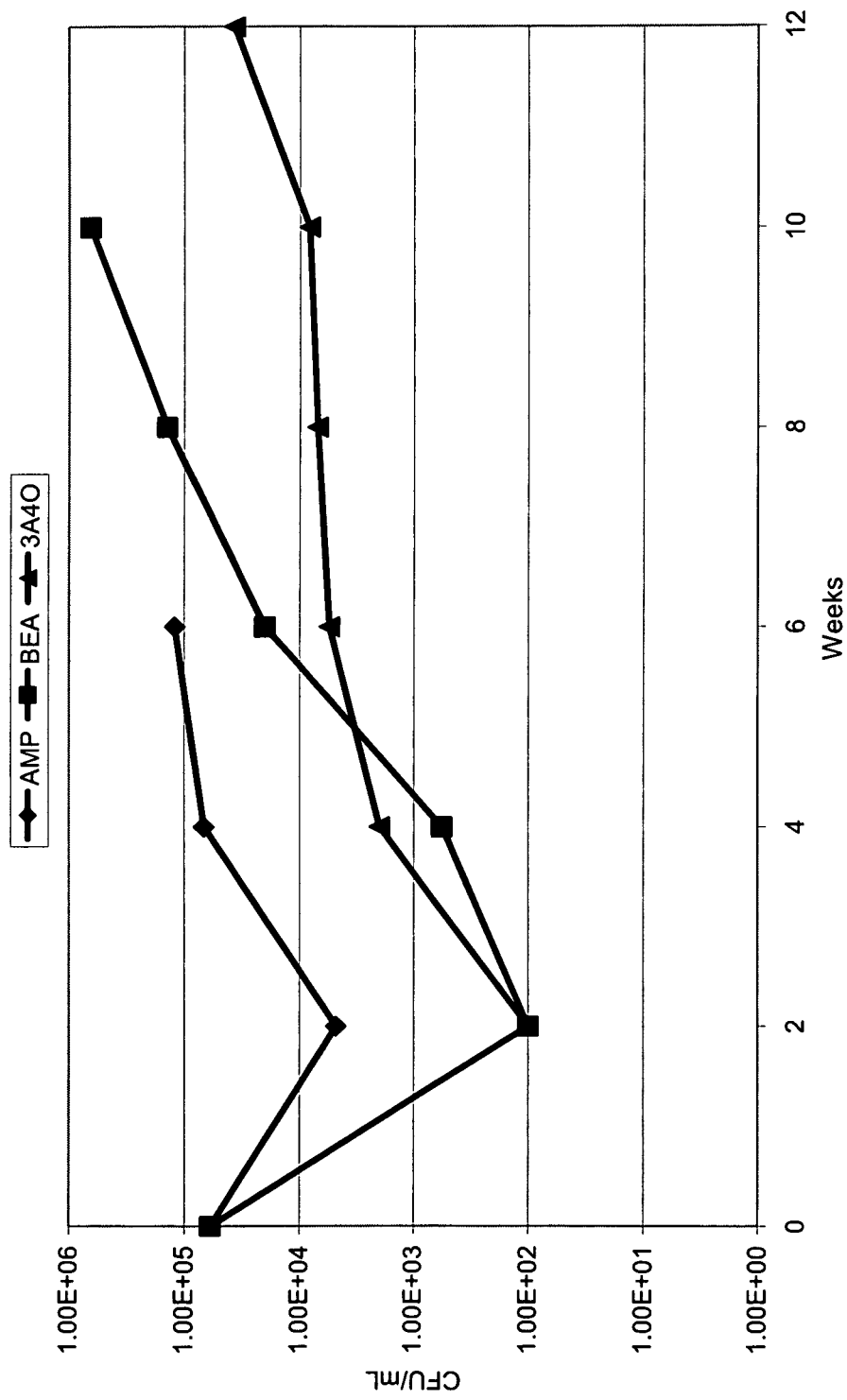
Figure 4 - Fluids Preserved with Triazine - Fungal Data

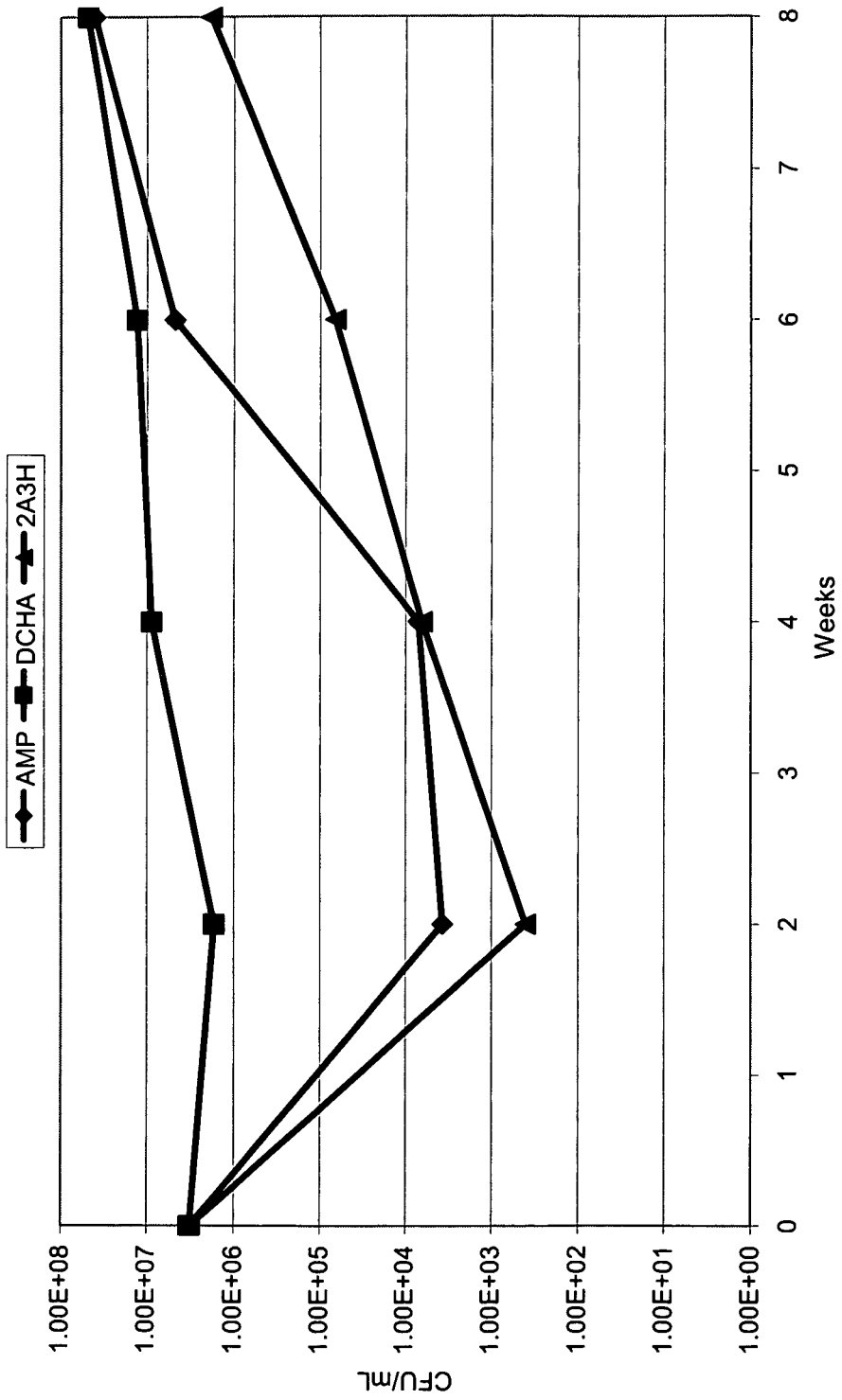

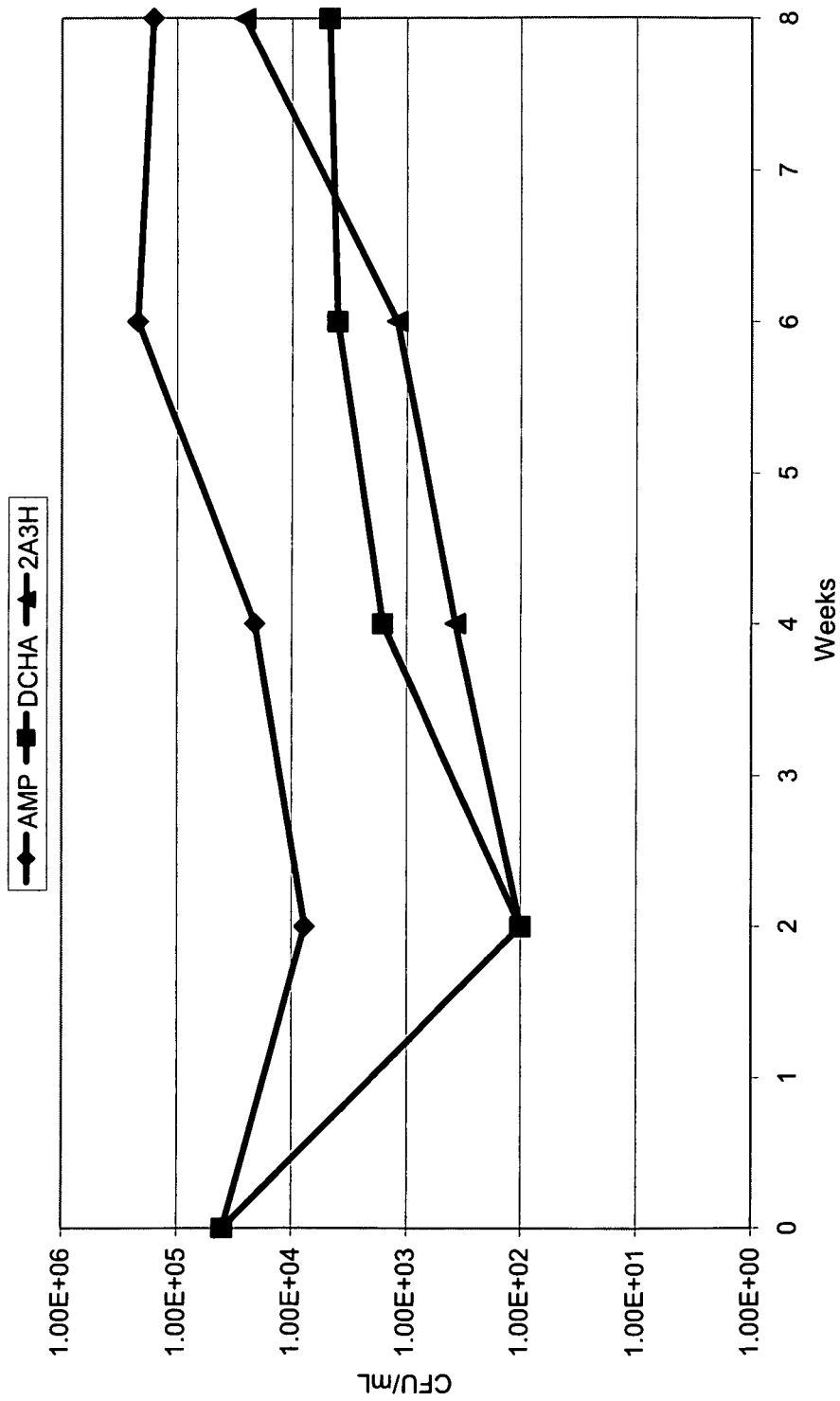

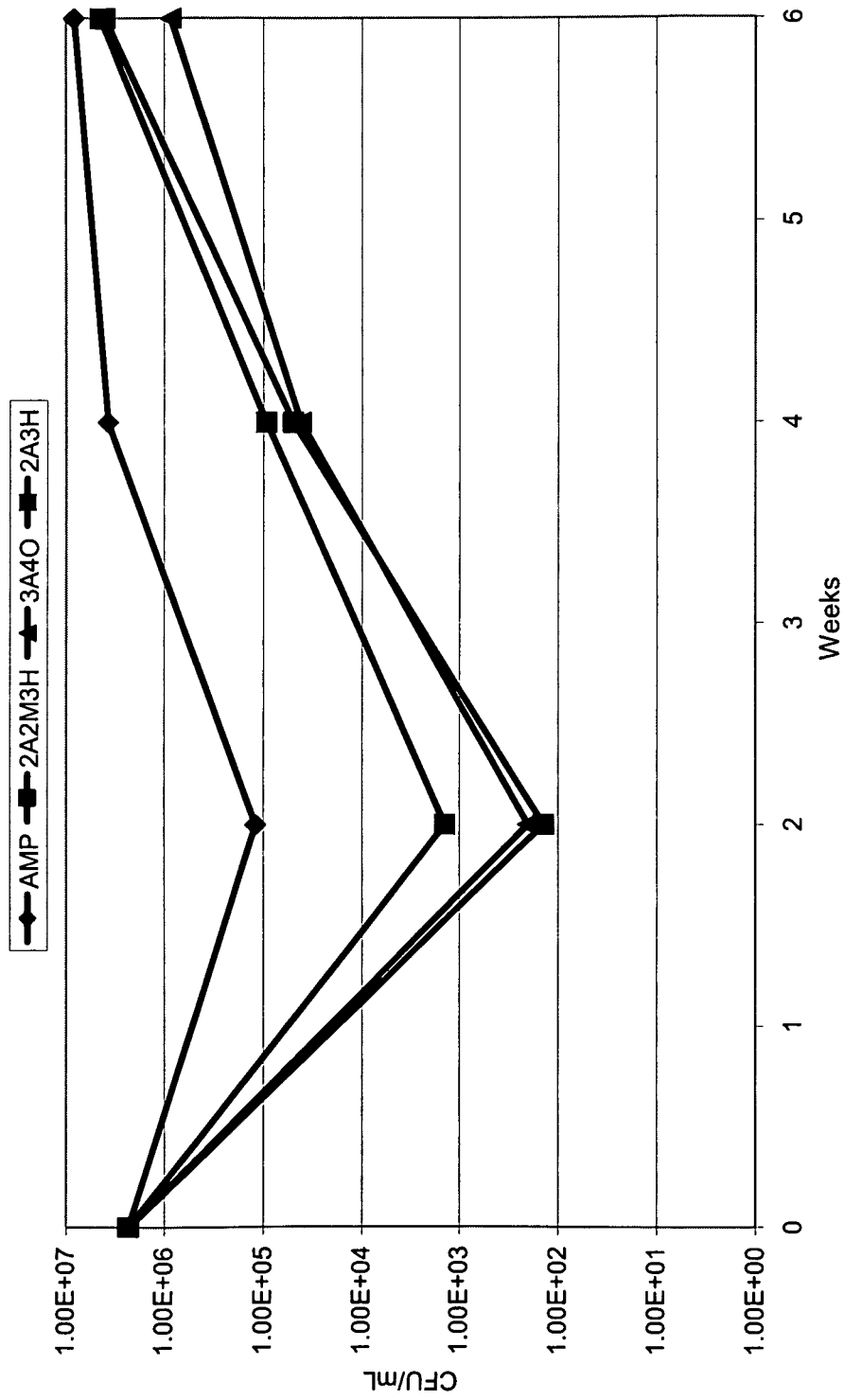
Figure 7 - Fluids Preserved with Triazine - Mycobacterial Data

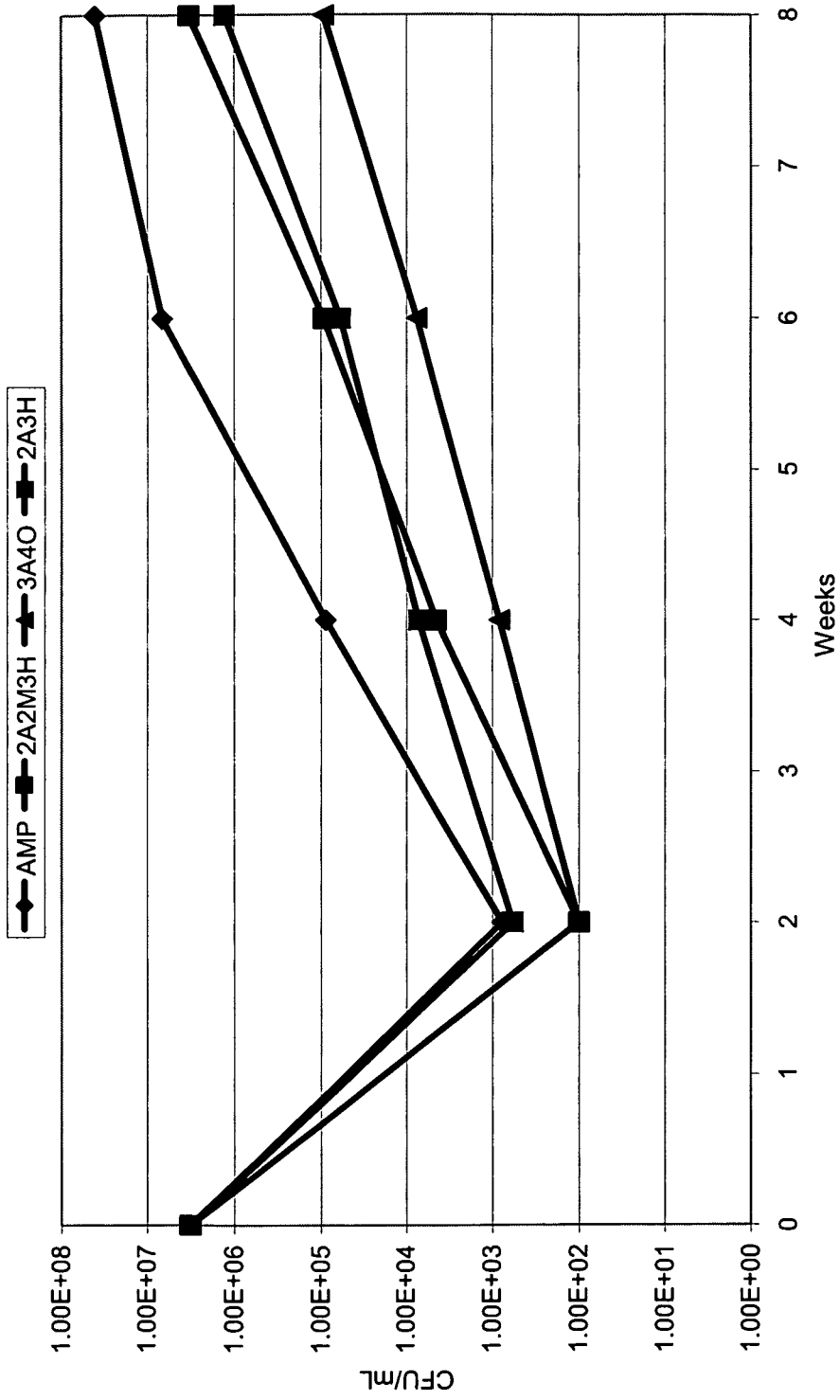

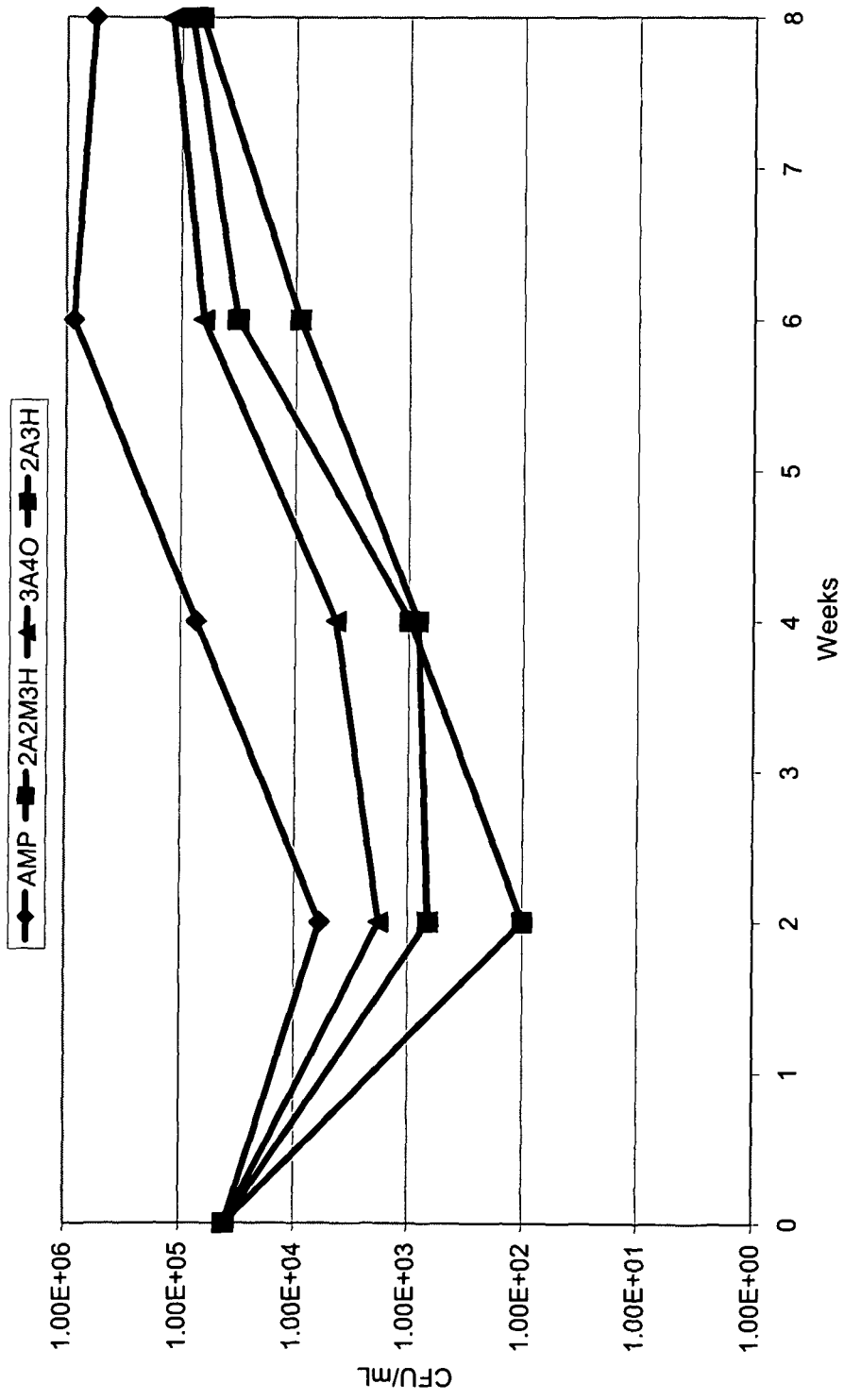

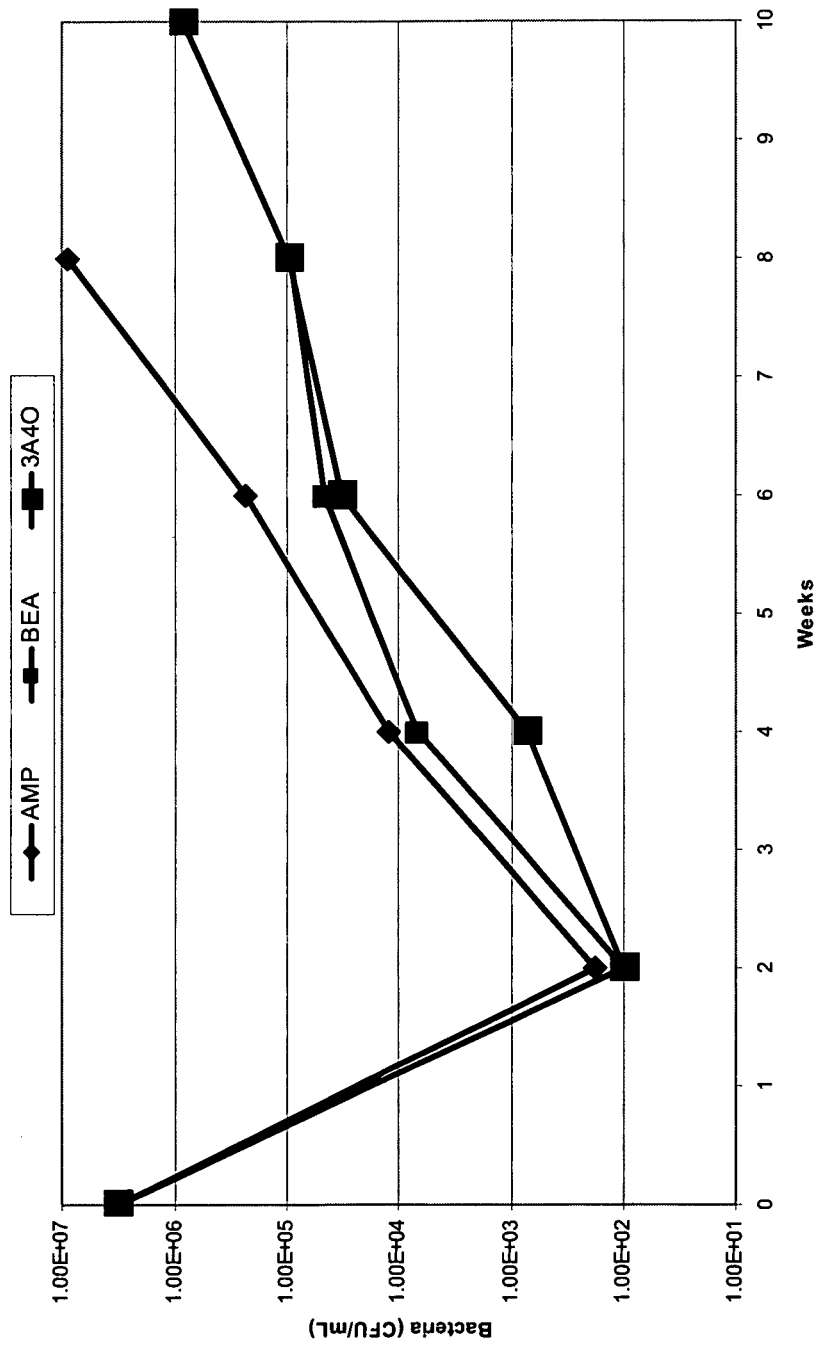
Figure 10 - Fluids Preserved with BIOBAN P-1487 - Bacterial Data

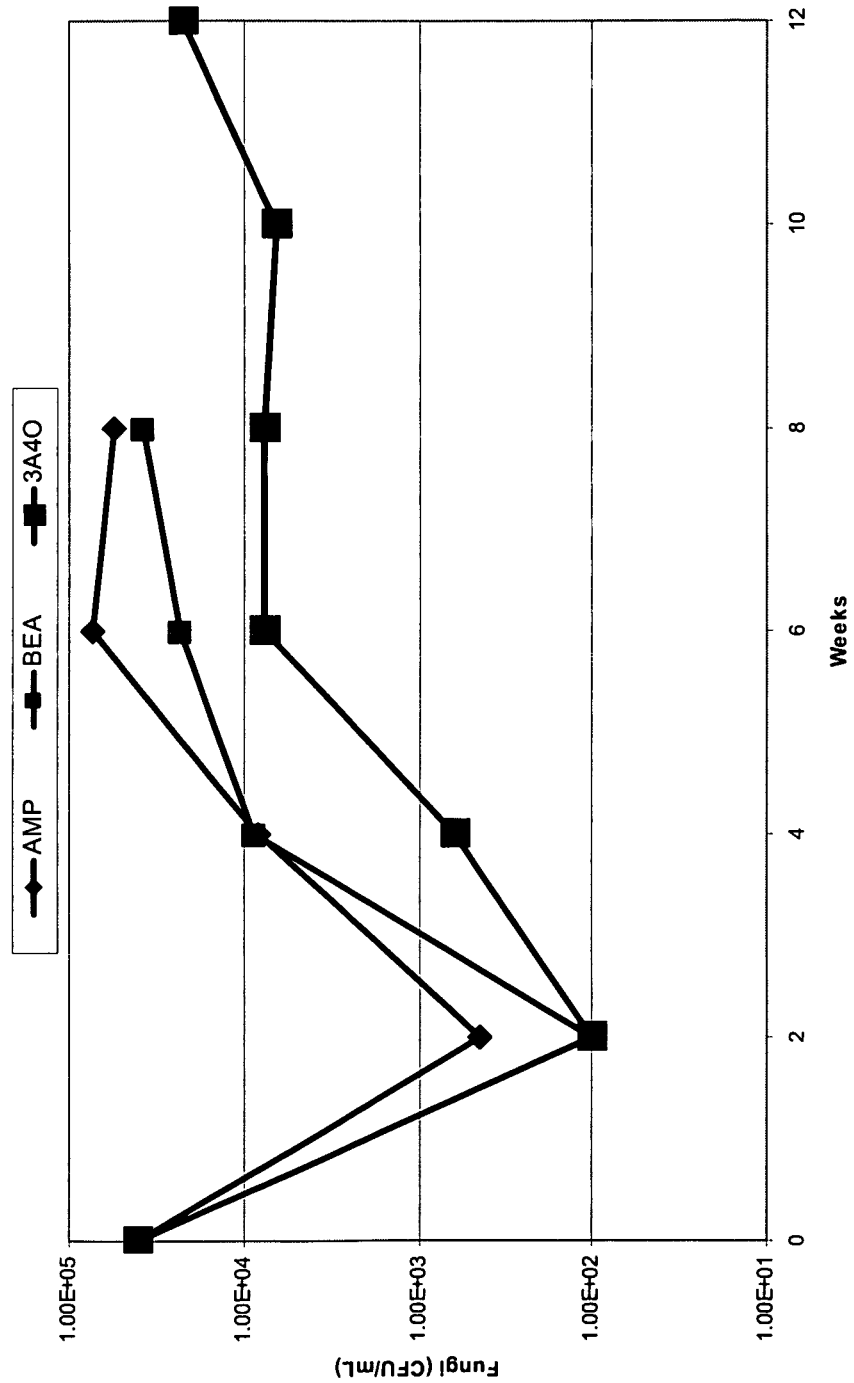

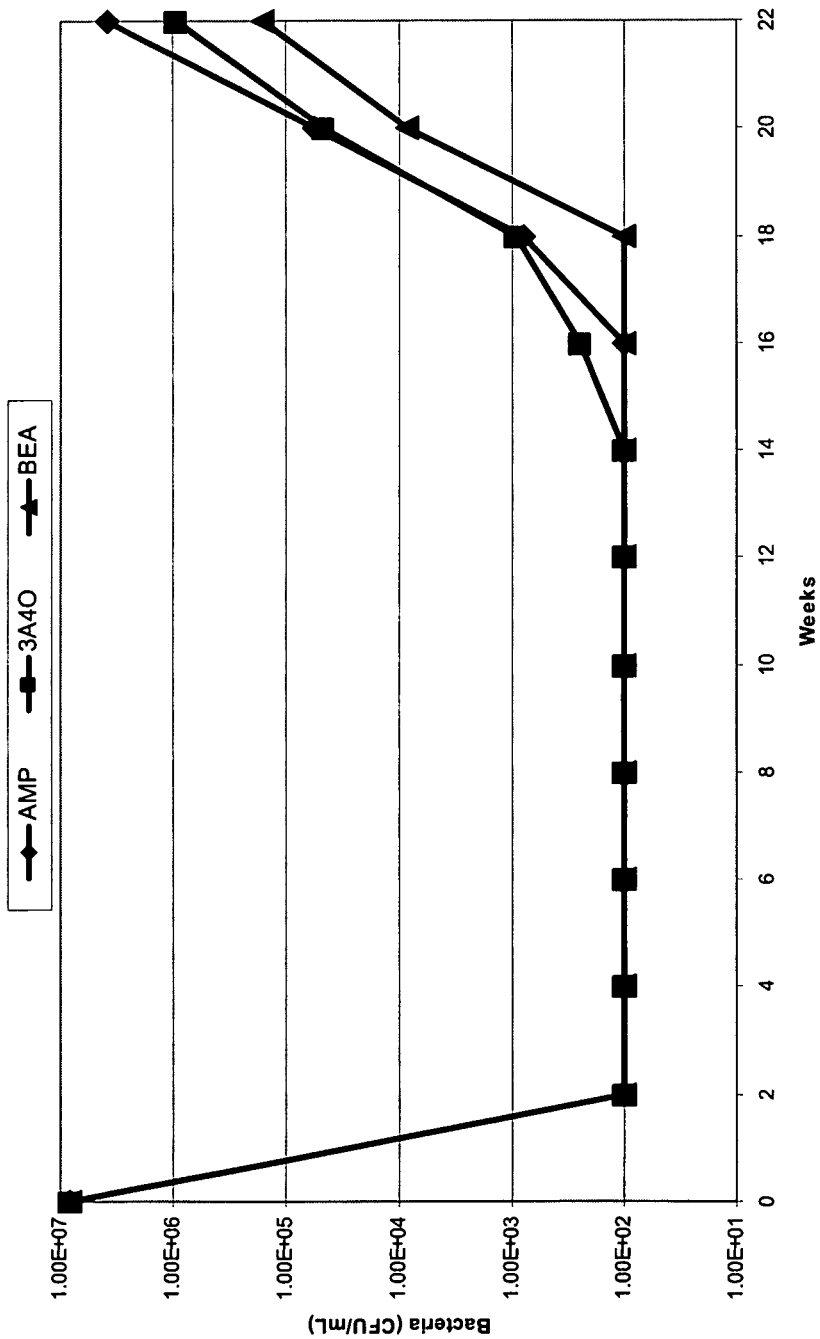

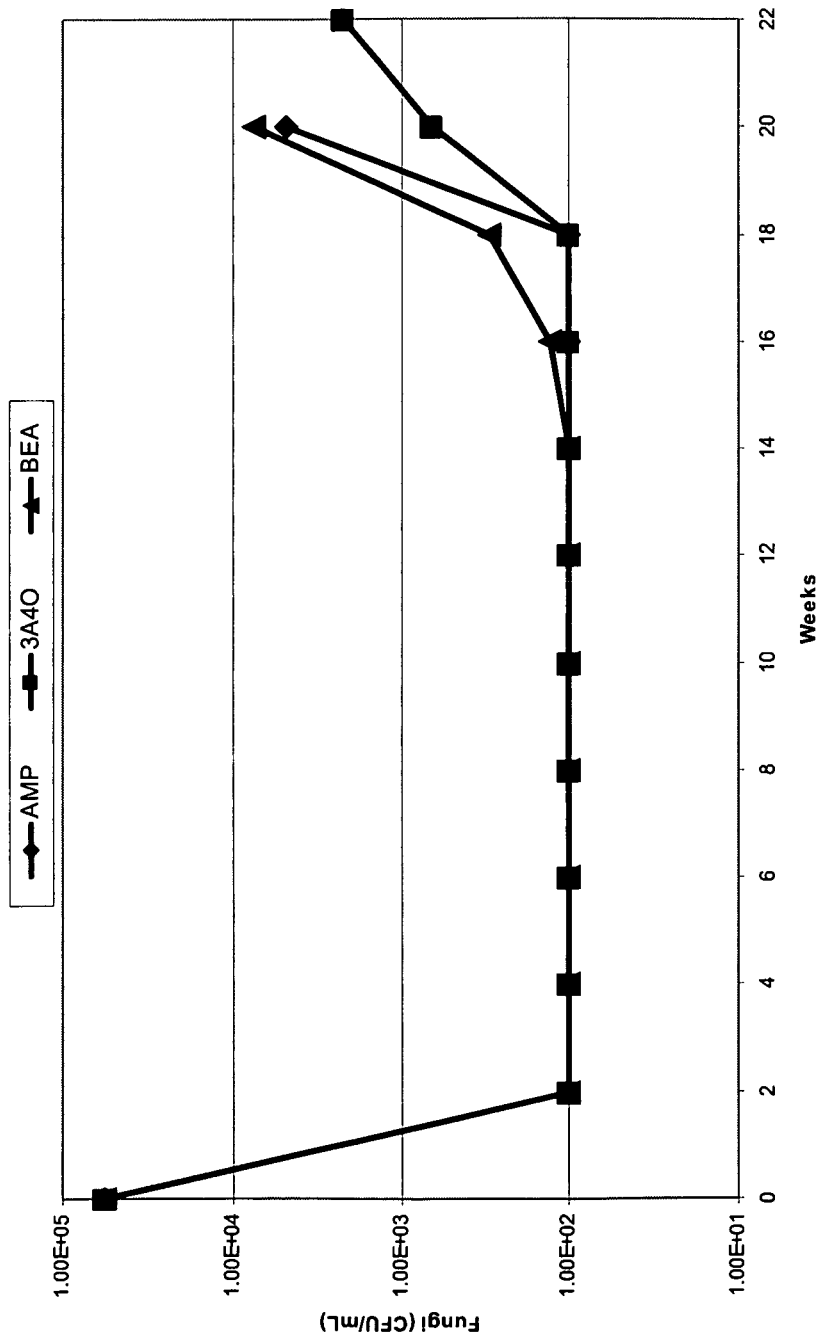

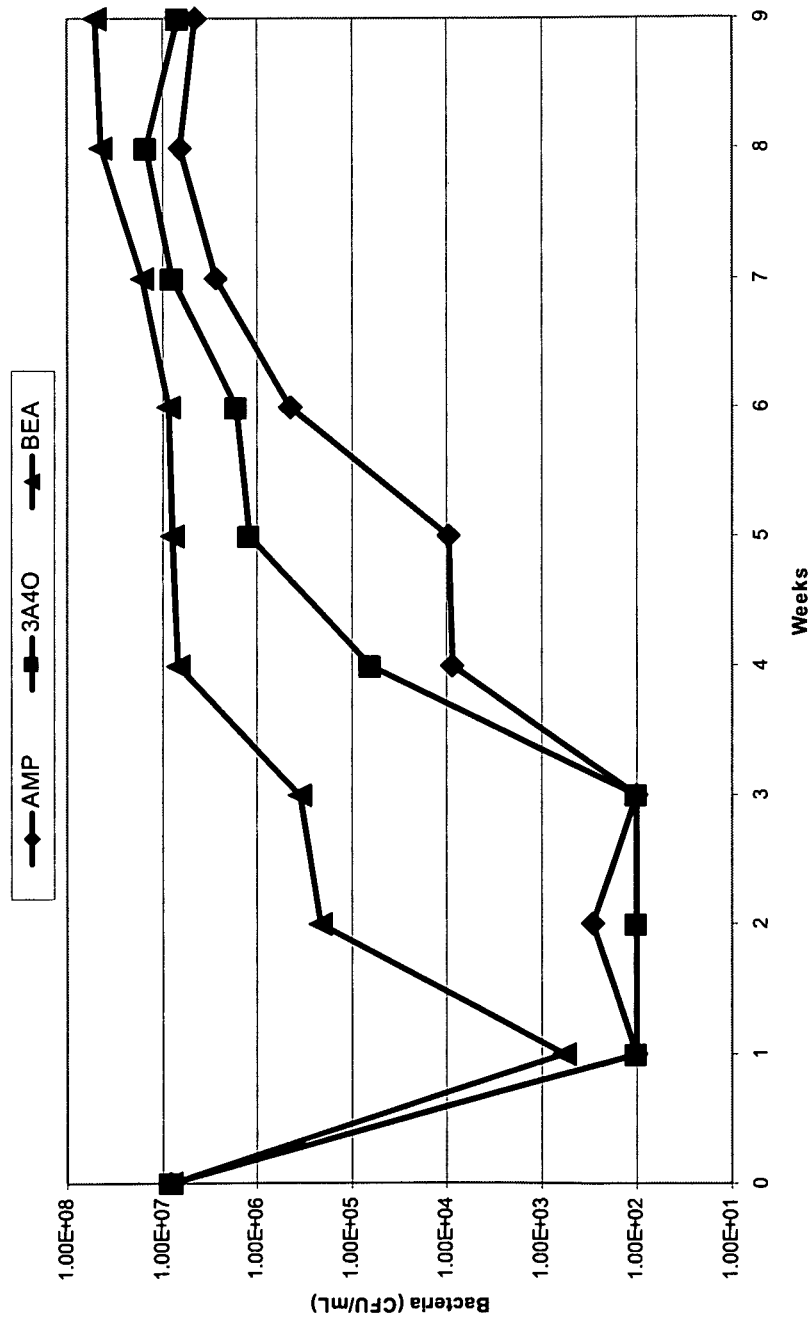
Figure 14 - Fluids Preserved with BIT & IPBC - Bacterial Data

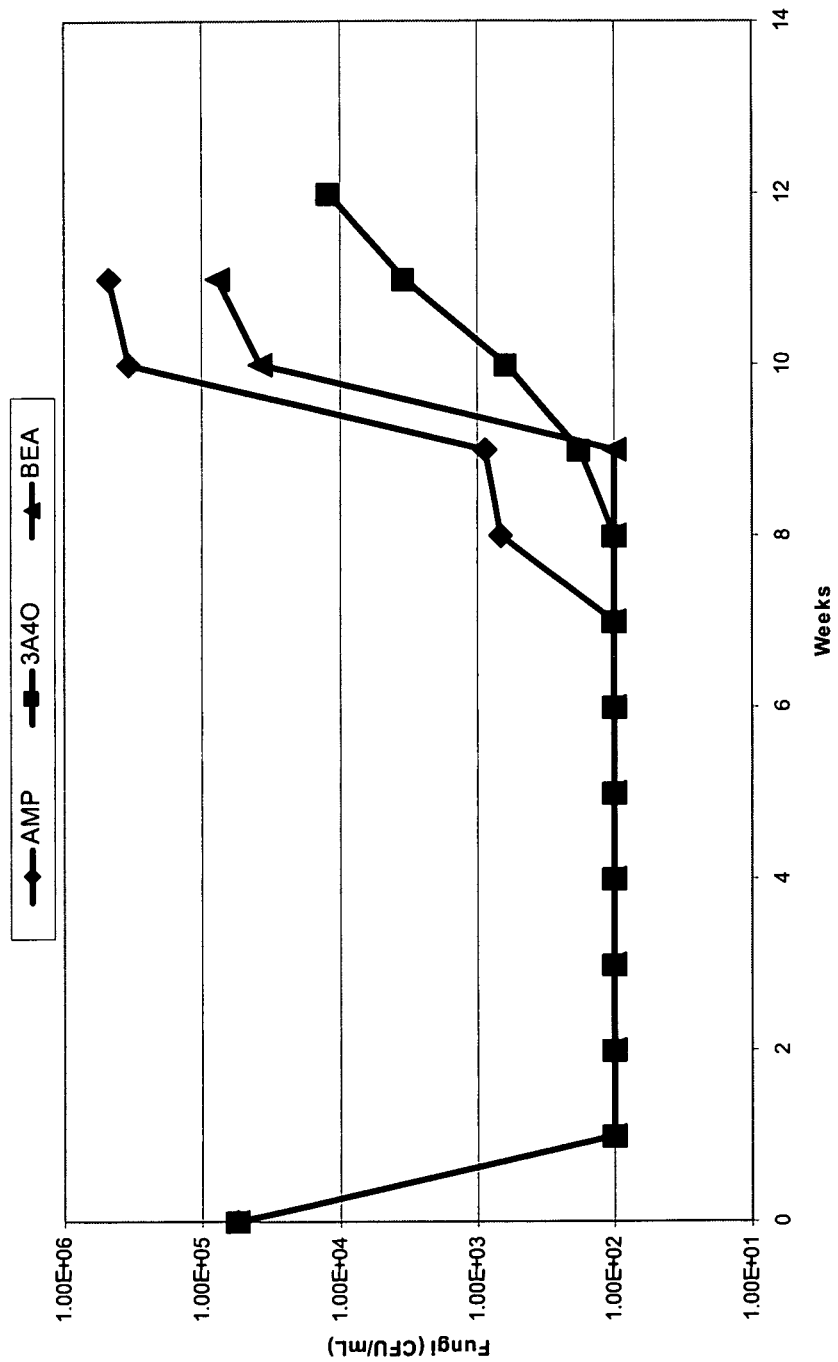

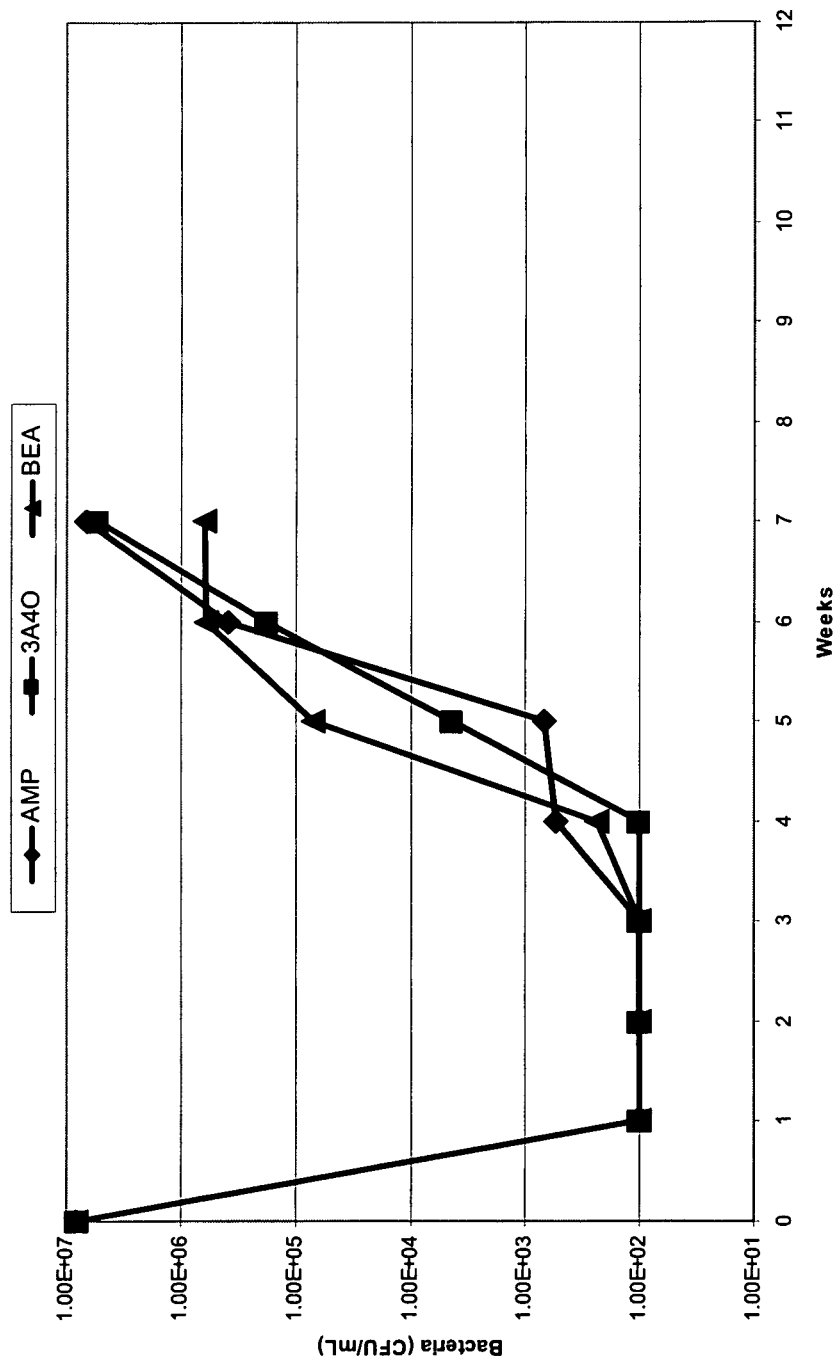

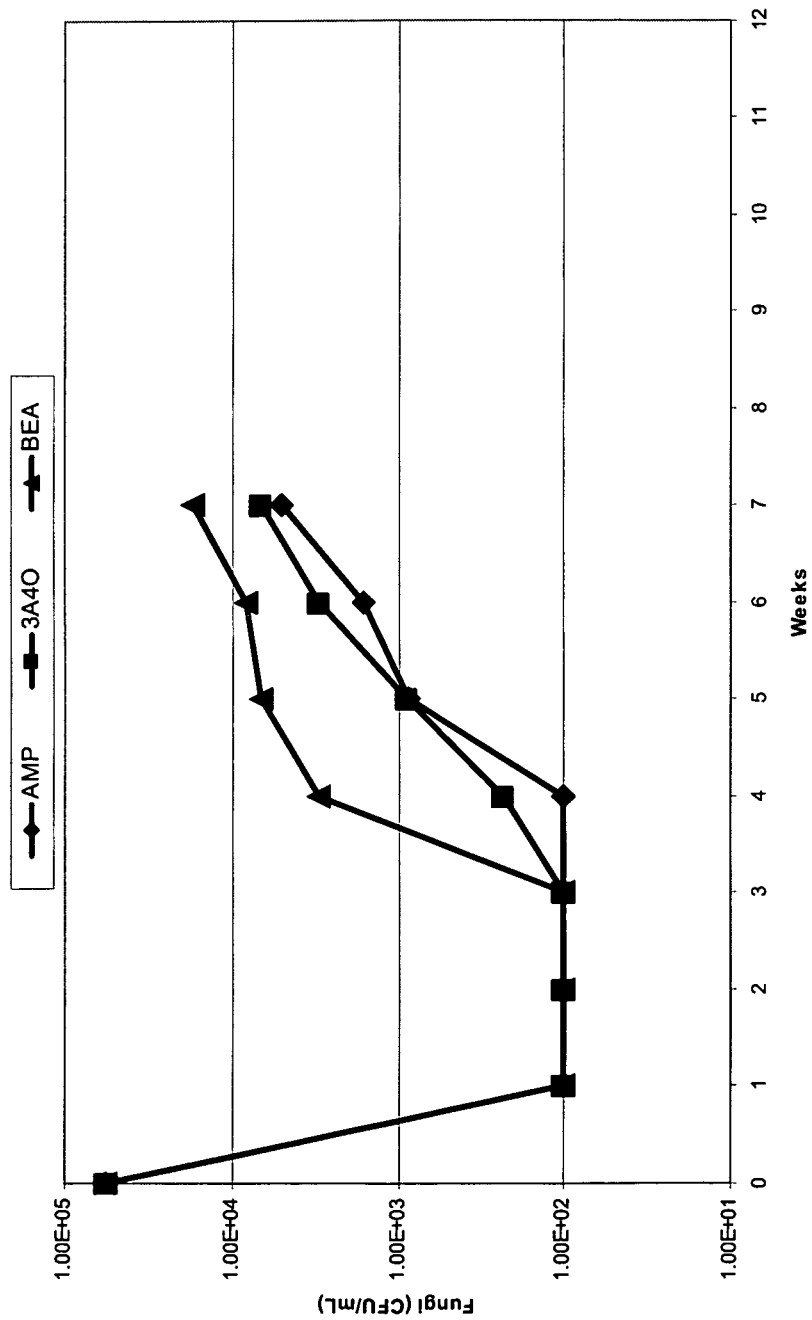

AMINOALCOHOL AND BIOCIDE COMPOSITIONS FOR AQUEOUS BASED SYSTEMS

CROSS-REFERENCE TO RELATED APPLICATIONS

This is a §371 application of PCT International Patent Application Number PCT/US2007/087365 filed Dec. 13, 2007, and claims the benefit of priority of U.S. provisional application Ser. No. 60/880,333, filed Jan. 12, 2007, and U.S. provisional application Ser. No. 60/899,450, filed Feb. 5, 2007, each of which is incorporated herein by reference in its entirety.

FIELD OF THE INVENTION

The invention relates to biocidal compositions for use in aqueous-based systems such as metalworking fluids, to methods of use, and to novel amino alcohol compounds.

BACKGROUND OF THE INVENTION

Short chain amino alcohols are used commercially in a wide variety of applications because of their anti-corrosion, neutralization and pH adjustment and maintenance properties. One such application is in metalworking fluids.

Metalworking fluids ("MWFs") are used throughout the manufacturing industry for their coolant, lubricant, and corrosion resistant properties during operations such as metal cutting, grinding, boring, drilling, and turning. These fluids are made of mixtures of oils, detergents, surfactants, lubricants, anti-corrosion agents, water and other ingredients, and usually contain amino alcohols for maintaining alkaline pH and for neutralizing acid functional components in the MWFs.

Companies producing and using water-miscible MWFs want them to last a long time in order to minimize operating and waste disposal costs as well as loss of production time. Water-miscible MWFs containing amino alcohols as corrosion inhibitors are degraded over time by processes such as microbial degradation. Microbial growth is often directly related to fluid performance because microbes feed on the active ingredients in the fluid.

An industry need exists for amino alcohol components which do not support microbial growth and which maintain performance over a long time period. A need also exists for amino alcohols which, although not biocidal themselves, enhance the performance of a wide range of biocides used in water-based MWFs. While secondary amines are in common use, primary amines that fulfill the above purposes would be desirable because of regulatory restrictions on use of secondary amines in certain parts of the world.

The present invention addresses the above-described needs.

BRIEF SUMMARY OF THE INVENTION

In one aspect, the invention provides a biocidal composition. The composition comprises a biocidal agent and a primary amino alcohol compound that is non-biocidal, wherein the primary amino alcohol compound is of the formula (I):

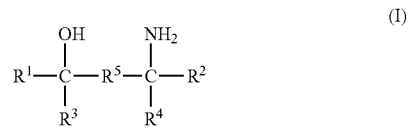

wherein $R^1$, $R^2$, $R^3$, $R^4$, and $R^5$ are as defined below.

In another aspect, the invention provides aqueous-based systems (i.e. systems containing sufficient water to support microbial growth), such as metalworking fluids, comprising the biocidal compositions disclosed herein.

In another aspect, the invention provides a method of inhibiting the growth of microorganisms in an aqueous-based system comprising adding to said system an effective amount of a composition as described herein.

In a further aspect, the invention provides novel amino alcohol compounds and salts thereof.

BRIEF DESCRIPTION OF THE FIGURES

FIG. 1 is a graph showing bacterial growth data for an 8% amino alcohol-based fluid that does not contain biocide.

FIG. 2 is a graph showing fungal growth data for an 8% amino alcohol-based fluid that does not contain biocide.

FIG. 3 is a graph showing bacterial growth data for an 8% amino alcohol-based fluid containing a triazine biocide.

FIG. 4 is a graph showing fungal growth data for an 8% amino alcohol-based fluid containing a triazine biocide.

FIG. 5 is a graph showing bacterial growth data for an 8% amino alcohol-based fluid containing benzisothiazolinone biocide.

FIG. 6 is a graph showing fungal growth data for an 8% amino alcohol-based fluid containing benzisothiazolinone biocide.

FIG. 7 is a graph showing mycobacterial growth data for an 8% amino alcohol-based fluid containing a triazine biocide.

FIG. 8 is a graph showing bacterial growth data in a 4% amino alcohol-based fluid containing a triazine biocide.

FIG. 9 is a graph showing fungal growth data in a 4% amino alcohol-based fluid containing a triazine biocide.

FIG. 10 is a graph comparing enhancement, with an aminoalcohol of the invention compared to two conventional aminoalcohols, of BIOBAN P-1487 (a combination of 4-(2-nitrobutyl)-morpholine with 4,4'-(2-ethyl-2-nitrotrimethylene)dimorpholine) against bacteria.

FIG. 11 is a graph comparing enhancement, with an aminoalcohol of the invention compared to two conventional aminoalcohols, of BIOBAN P-1487 (a combination of 4-(2-nitrobutyl)-morpholine with 4,4'-(2-ethyl-2-nitrotrimethylene)dimorpholine) against fungi.

FIG. 12 is a graph comparing enhancement, with an aminoalcohol of the invention compared to two conventional aminoalcohols, of a triazine/IPBC biocide blend against bacteria.

FIG. 13 is a graph comparing enhancement, with an aminoalcohol of the invention compared to two conventional aminoalcohols, of a triazine/IPBC biocide blend against fungi.

FIG. 14 is a graph comparing enhancement, with an aminoalcohol of the invention, compared to two conventional aminoalcohols, of benzisothiazolinone (BIT) against bacteria.

FIG. 15 is a graph comparing enhancement, with an aminoalcohol of the invention, compared to two conventional aminoalcohols, of benzisothiazolinone (BIT) against fungi.

FIG. 16 is a graph comparing enhancement, with an aminoalcohol of the invention compared to two conventional aminoalcohols, of a chloromethylisothiazolinone/methylisothiazolinone (CMIT/MIT) blend against bacteria.

FIG. 17 is a graph comparing enhancement, with an aminoalcohol of the invention compared to two conventional aminoalcohols, of a chloromethylisothiazolinone/methylisothiazolinone (CMIT/MIT) blend against fungi.

DETAILED DESCRIPTION OF THE INVENTION

The present inventors have discovered that primary amino alcohols containing at least 6 and preferably up to 12 carbon atoms, although themselves not biocidal, surprisingly enhance the performance of biocides used in various media. As noted above, one aspect of the invention is the provision of a biocidal composition. The biocidal composition comprises a biocidal agent and a non-biocidal primary amino alcohol compound of formula (I).

The biocidal agent (also referred to herein as "biocide" or "preservative") is any substance that kills or inhibits the growth of microorganisms such as bacteria, molds, slimes, fungi, algae and the like, including formaldehyde based and non-formaldehyde based biocidal agents. Specific, non-limiting, examples of suitable agents include: triazines such as 1,3,5-tris-(2-hydroxyethyl)-s-triazine and trimethyl-1,3,5-triazine-1,3,5-triethanol, an example being GROTAN by Troy Corporation, iodopropynylbutylcarbamate, such as POLYPHASE supplied by Troy Corporation, 1,2-benzisothiazolin-3-one, such as BIOBAN BIT marketed by The Dow Chemical Company, 4,4-dimethyloxazolidine, an example being BIOBAN CS-1135 from The Dow Chemical Company, 7-ethyl bicyclooxazolidine, marketed as BIOBAN CS-1246 by The Dow Chemical Co., a combination of 4-(2-nitrobutyl)-morpholine with 4,4'-(2-ethyl-2-nitrotrimethylene)dimorpholine, marketed as BIOBAN P-1487 by The Dow Chemical Co., 2-methyl-4-isothiazolin-3-one, a combination of 5-chloro-2-methyl-4-isothiazolin-3-one with 2-methyl-4-isothiazolin-3-one, such as the KATHON brand supplied by Rohm & Haas Corporation, 2-bromo-2-nitro-1,3-propanediol, octylisothiazolinone, dichloro-octylisothiazolinone, dibromo-octylisothiazolinone, phenolics such as o-phenylphenol and p-chloro-m-cresol and their corresponding sodium and/or potassium salts, sodium pyrithione, zinc pyrithione, n-butyl benzisothiazolinone, 1-(3-chloroallyl)-3,5,7-triaza-1-azoniaadamantane chloride, chlorothalonil, carbendazim, diiodomethyltolylsulfone, 2,2-dibromo-3-nitrilopropionamide (DBNPA), glutaraldehyde, N,N'-Methylene-bis-morpholine, ethylenedioxy methanol (e.g. Troyshield B7), phenoxyethanol, (e.g. Comtram 121), tetramethylol acetylenediurea (e.g. Protectol TD), dithiocarbamates, 2,6-Dimethyl-m-dioxan-4-ol acetate (e.g Bioban DXN), dimethylol-dimethyl-hydantoin, tris(hydroxymethyl) nitromethane, bicyclic oxazolidines (e.g. Nuospet 95), and mixtures of two or more thereof. In the invention, non-formaldehyde agents are preferred because of industry preference in developed countries, however, one of the advantages of the invention is that it is applicable to a wide variety of biocides.

Particularly preferred biocides are triazines, substituted oxazolidines, benzisothiazolinone, iodopropynylbutylcarbamate, sodium pyrithione, octylisothiazolinone, a combination of 5-chloro-2-methyl-4-isothiazolin-3-one with 2-methyl-4-isothiazolin-3-one, phenolics, glutaraldehyde, 2,2-dibromo-3-nitrilopropionamide (DBNPA), 1-(3-chloroallyl)-3,5,7-triaza-1-azoniaadamantane chloride, N,N'-Methylene-bis-morpholine, and mixtures of two or more thereof.

The primary amino alcohol compound is of the formula (I):

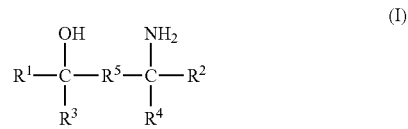

wherein $R^1$ and $R^3$ are each independently H, linear or branched alkyl, alkenyl, alkynyl groups, cycloalkyl, or aryl (preferably phenyl), or $R^1$, $R^3$ and the carbon to which they are attached form a cycloalkyl ring, $R^2$ and $R^4$ are each independently H or alkyl, provided that $R^2$ and $R^4$ together contain 2 or fewer carbon atoms; and $R^5$ is absent or is a $C_1$-$C_{10}$ aliphatic alkylene (bridging alkyl), arylene (preferably phenyl), -arylene-alkylene-, or -alkylene-arylene- (e.g., benzyl, phenethyl, and the like); wherein alkyl, cycloalkyl, alkylene, aryl, and arylene are optionally substituted with alkyl or phenyl, and wherein the compound of formula (I) contains at least 6 carbon atoms and preferably no more than 12 carbon atoms.

In some preferred embodiments of formula (I), $R^1$ is $C_1$-$C_6$ alkyl, more preferably straight chain or branched propyl, butyl, pentyl, or hexyl, and particularly preferably n-butyl.

In some further preferred embodiments of formula (I), $R^2$ is methyl. In other preferred embodiments, $R^2$ is ethyl. In still further preferred embodiments, $R^2$ is H.

In further preferred embodiments, $R^3$ is hydrogen and $R^4$ is hydrogen.

Also preferably, $R^5$ is absent (i.e., is a bond) or is a methylene or ethylene bridge.

Further preferred aminoalcohols of formula I include compounds of formula (II):

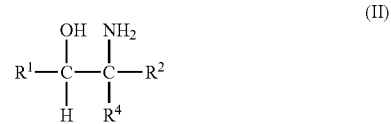

wherein $R^1$ is $C_2$-$C_6$ alkyl; and $R^2$ and $R^4$ are each independently H or $C_1$-$C_2$ alkyl, wherein $R^2$ and $R^4$ together contain 2 or fewer carbon atoms, and wherein the compound contains at least 6 carbon atoms.

Particularly preferred primary amino alcohols for use in the invention include: 2-amino-3-hexanol, 2-amino-2-methyl-3-hexanol, 3-amino-4-octanol, 2-amino-2-methyl-3-heptanol, 2-amino-4-ethyl-3-octanol, 2-amino-3-heptanol, 2-amino-1-phenylbutanol, and mixtures thereof. Especially preferred is 3-amino-4-octanol.

The amino alcohols may be used in the form of acid salts. Suitable salts include, but are not limited to, boric acid, lactic acid, pelargonic acid, nonanoic acid, neodecanoic acid, sebacic acid, azelaic acid, citric acid, benzoic acid, undecylenic acid, lauric acid, myristic acid, stearic acid, oleic acid, tall oil fatty acid, ethylenediaminetetraacetic acid and like materials.

The biocidal compositions may include additional additives, including, for instance other corrosion inhibitors, such as 2-amino-2-methyl-1-propanol (AMP), 2-amino-1-ethanol (MEA), 1-amino-2-propanol (MIPA), bis(2-hydroxypropyl) amine (DIPA), tris(2-hydroxypropyl)amine (TIPA), bis(2-hydroxyethyl)amine (DEA), tris(2-hydroxyethyl)amine (TEA), 2-(2-aminoethoxy)ethanol (DGA), or mixtures thereof. Less preferred of these additional additives are the secondary amines, because these are more heavily regulated in various parts of the world.

As noted above, the amino alcohols are not biocidal, i.e., they do not significantly inhibit biocidal growth. That is, at typical use levels (e.g., up to 4000 ppm in diluted MWF) these materials do not inhibit microbial growth to the extent of recognized biocidal agents intended for this purpose. This is apparent when comparing data for one of the compounds of the invention (3A4O) in an unpreserved fluid (FIG. 1), with that for an amino alcohol not of the invention (AMP) in combination with a recognized biocidal agent (triazine) in the same fluid (FIG. 3).

The amino alcohol compounds may be readily prepared by a person of ordinary skill in the art using techniques well known in the art. For example, such compounds may be prepared by the reaction of nitroalkanes with aromatic aldehydes or ketones or more preferably with aliphatic aldehydes, followed by catalytic hydrogenation.

The composition of the invention contains the amino alcohol compound and the biocide at various weight ratios, which will depend for instance on the particular biocide being used, and the particular aqueous medium. The ratio can be readily determined by a person of ordinary skill in the art. By way of a general example, the weight ratio of amino alcohol to biocide will generally be about 0.25:1 or greater and preferably about 500:1 or less. Further preferred amounts are described below.

Some of the amino alcohols described herein are novel. Thus, a further aspect of the invention is the provision of novel amino alcohol compounds and salts thereof. The novel compounds are, 2-amino-2-methyl-3-heptanol, and 2-amino-4-ethyl-3-octanol.

As noted above, the compositions containing biocide of the invention are useful for inhibiting the growth of microorganisms in aqueous-based systems. Preferred systems for which the compositions of the invention are particularly suitable are metalworking fluids (MWFs). The compositions may be used with all types of MWFs, including soluble oil, synthetic, semi-synthetic, non-synthetic, emulsion forming, and non-emulsion forming fluids. Typically, MWFs are provided in a concentrated form and are diluted with water prior to use. The invention encompasses metalworking fluid concentrates containing the biocidal composition, diluted metalworking fluids thereof, metalworking fluid concentrates pre-diluted with water, as well as non-concentrate metalworking fluids to which the biocidal composition is added. Typically, 1 part by weight of a MWF concentrate is diluted with between about 10 and about 100 parts of water, more preferably 10 to 50 parts of water and most preferably with 15 to 30 parts of water.

Metalworking fluids and concentrates containing the biocidal compositions of the invention may contain hydrocarbon oils, which may be synthetic or non-synthetic. Examples of synthetic and non-synthetic oils commonly used include, for instance, mineral oils, vegetable oils, animal-derived oils, and synthetic polymers/copolymers. Specific examples of such oils include, without limitation, severely hydrotreated naphthenic and paraffinic oils, soybean oil and polyglycol block co-polymers.

Optional other additives well known in the art that may be included in the metalworking fluid (whether synthetic or non-synthetic) include, for example colorants; agents that alter viscosity; emulsifying agents (not generally required for synthetic MWFs because these are non-emulsion systems); buffers; solubilizers; anti-oxidants; anti-foaming agents; surfactants and antimisting agents and extreme pressure additives. The metalworking fluid will normally contain agents for inhibiting corrosion such as alkaline and amino alcohol salts (in addition to the compositions of the invention) of organic acids, sulfonates, amines, amides, and organic borate compounds.

By way of more specific example, emulsion-forming metalworking fluid concentrates, commonly known as soluble oils and semi-synthetics, typically contain the following types of components: Low viscosity hydrocarbon oils and synthetic lubricants such as polyalkylene glycols; Emulsifiers such as low molecular weight sodium petroleum sulfonates, alkanolamides, amine-fatty acid salts and non-ionic surfactants such as nonylphenol ethoxylates; Corrosion inhibitors such as medium-high molecular weight sodium petroleum sulfonates, alkanolamides, and amino alcohol salts of various organic and inorganic acids including nonanoic, neodecanoic, sebacic, oleic, tall oil, boric and many others; Coupling agents including glycol ethers and higher alcohols and glycols. Examples from each class include propylene glycol n-butylether, hexanol and hexylene glycol; and Lubricity and extreme pressure agents including fatty esters, phosphate esters, chlorinated fatty acids and sulfurized fatty acids By way of further example, non-emulsion forming metalworking fluid concentrates, commonly known as synthetic or solution synthetic fluids, typically contain the following: Lubricity and extreme pressure agents such as inversely soluble esters, phosphate esters, chlorinated fatty acids and polyalkylene glycols; Amine salts of organic and inorganic acids including pelargonic, neodecanoic, azelaic, dodecanoic, dodecanedioic, boric, lactic and many others. These materials are corrosion inhibitors.

The concentration of neat amino alcohol compound in the MWF concentrate (i.e., prior to dilution) is preferably at least about 1% by weight, more preferably at least about 2%, and even more preferably at least about 3%. Also preferably, the concentration is no more than about 20%, more preferably no more than about 12%, and even more preferably, no more than about 8%. In other embodiments, the concentration is in the range of about 1-20%, more preferably about 2-12%, and most preferably about 3-8%.

The preferred active concentration ranges for the biocide in the MWF concentrate varies depending on the biocide being used, but can be readily determined by a person of ordinary skill in the art. By way of example, the concentration is preferably at least about 0.01% by weight and no more than about 5% by weight.

By way of example for specific biocides, 1,3,5-tris(2-hydroxyethyl)-s-triazine is preferably used in the active range of 0.76 to 3% by weight, with a most preferred range of 1.1 to 3%, iodopropynylbutylcarbamate is used in the range of 0.2 to 0.6%, with a most preferred range of 0.3 to 0.6%, 1,2-benzisothiazolinone is used in the range of 0.08 to 0.36%, with a most preferred range of 0.16 to 0.36%, 4,4-dimethyloxazolidine is used in the range of 0.78 to 3.1% with a most preferred range of 1.2 to 3.1%, 7-ethyl bicycooxazolidine is used in the range 1 to 4% with a most preferred range of 1.5 to 4%, a combination of 4-(2-nitrobutyl)-morpholine with 4,4'-(2-ethyl-2-nitrotrimethylene)dimorpholine is used in the range of 1 to 4% with a most preferred range of 1.5 to 3%, and a combination of 5-chloro-2-methyl-4-isothiazolin-3-one with 2-methyl-4-isothiazolin-3-one is used in the range of 0.01% to 0.08% of with a most preferred range of 0.05% to 0.08%.

In the final diluted MWF, the use range of neat amino alcohol is preferably between about 0.05% to 1.0%, with a preferred range of 0.1% to 0.6%, and a most preferred range of 0.15% to 0.4%. The biocide agent is preferably used in the range (active basis at dilution) of 0.04% to 0.3% 1,3,5-tris(2-hydroxyethyl)-s-triazine with a preferred range of 0.06% to 0.15%, 0.01% to 0.04% iodopropynylbutylcarbamate with a preferred range of 0.015% to 0.03%, 0.004% to 0.03% 1,2-benzisothiazolin-3-one with a preferred range of 0.008% to 0.02%, 0.04% to 0.3% 4,4-dimethyloxazolidine with a preferred range of 0.06% to 0.2%, 0.05% to 0.3% 7-ethyl bicyclooxazolidine with a preferred range of 0.075% to 0.2%, 0.05% to 0.3% of a combination of 4-(2-nitrobutyl)-morpholine with 4,4'-(2-ethyl-2-nitrotrimethylene)dimorpholine with a preferred range of 0.075% to 0.2%, 0.002% to 0.005% of a combination of 5-chloro-2-methyl-4-isothiazolin-3-one with 2-methyl-4-isothiazolin-3-one with a preferred range of 0.0025% to 0.004%.

Although metalworking fluids are the preferred system in which the biocidal compositions of the invention are used, the compositions are also useful in a wide variety of other systems which contain water or are intended to be diluted with water. For instance, the compositions may be used in aqueous emulsions such as latexes, water-based paints & coatings, caulks and adhesives, tape joint compounds, mineral slurries, water-cooling systems, personal care products, soaps and detergents, disinfectants, cleaners, and sanitizers, pesticide products, oilfield water and water-based fluids used in oilfield applications including drilling muds, fracturing fluids, and hydrotest fluids, and the like.

"Alkyl," as used in this specification, encompasses straight and branched chain aliphatic groups having from 1-8 carbon atoms, more preferably 1-6 carbon atoms. Preferred alkyl groups include, without limitation, methyl, ethyl, propyl, isopropyl, butyl, isobutyl, sec-butyl, tert-butyl, pentyl, and hexyl.

The term "alkenyl" as used herein means an unsaturated straight or branched chain aliphatic group with one or more carbon-carbon double bonds, having from 2-8 carbon atoms, and preferably 2-6 carbon atoms. Preferred alkenyl groups include, without limitation, ethenyl, propenyl, butenyl, pentenyl, and hexenyl.

The term "alkynyl" as used herein means an unsaturated straight or branched chain aliphatic group with one or more carbon-carbon triple bonds, having from 2-8 carbon atoms, and preferably 2-6 carbon atoms. Preferred alkynyl groups include, without limitation, ethynyl, propynyl, butynyl, pentynyl, and hexynyl.

An "alkylene" group is an alkyl as defined hereinabove, that is positioned between and serves to connect two other chemical groups. Preferred alkylene groups include, without limitation, methylene, ethylene, propylene, and butylene.

The term "cycloalkyl" as employed herein includes saturated and partially unsaturated cyclic hydrocarbon groups having 3 to 12 carbons, preferably 3 to 8 carbons, and more preferably 3 to 7 carbons. Preferred cycloalkyl groups include, without limitation, cyclopropyl, cyclobutyl, cyclopentyl, cyclopentenyl, cyclohexyl, cyclohexenyl, cycloheptyl, and cyclooctyl.

An "aryl" group is a C6-C12 aromatic moiety comprising one to three aromatic rings. Preferably, the aryl group is a C6-C10 aryl group. Preferred aryl groups include, without limitation, phenyl, naphthyl, anthracenyl, and fluorenyl. More preferred is phenyl.

Alkyl, cycloalkyl, and aryl (and their bridging derivatives alkylene, cycloalkylene, and arylene) are optionally substituted with one or more other alkyl (e.g., methyl, ethyl, butyl), phenyl, or both. When substituted, the number of carbons in the substituent are counted towards the 6-12 carbons of the compound.

Non-limiting examples of the invention are provided in the below.

EXAMPLES

Example A

Preparation and Evaluation of 3-Amino-4-Octanol Alkanolamine

Preparation of the 3-nitro-4-octanol from 1-nitropropane and valeraldehyde. A sample of 3-nitro-4-octanol was synthesized by the addition of 1-nitropropane (1-NP, 300 g, 3.37 mols) into a 1 liter 3-necked round-bottomed flask (RBF, 24/40, 29/42, 24/40) equipped with a thermocouple, a magnetic stirrer, a 500 ml addition funnel, a nitrogen inlet, and a glass stopper. This light yellow liquid was diluted by the addition of methanol (MeOH, 150 g) that resulted in an endotherm. The caustic catalyst was added (16 g of a 10% aqueous solution and 0.60 g of a 50% aqueous caustic solution, 1.9 g total, 1.4 mole %). This changed the reaction color to orange and resulted in a slight exotherm. The valeraldehyde (258 g, 3.00 mols, 0.89 equivalents) was charged to the addition funnel and slowly added to the 1-NP over 3 h. The heat of reaction raised the temperature to 40-45° C. Once the valeraldehyde addition was complete, the contents of the RBF were transferred into a 1 liter glass bottle, purged with nitrogen, and stored at ambient temperature. The reaction progress was monitored by gas chromatography. After 2 weeks the conversion reached 84 area % and the reaction was stopped by the addition of a 10% aqueous hydrochloric acid solution (19 ml). The resulting pH=1 solution was concentrated in vacuo (50° C./full vacuum/0.5 h) to remove solvent and residual reagents. The resulting olive green solution (491 g, 95 area % corrected purity, 89% yield) was filtered (0.5 micron), purged with nitrogen, and stored in the refrigerator until needed.

Catalytic hydrogenation of the 3-nitro-4-octanol to the 3-amino-4-octanol alkanolamine A sample of 3-amino-4-octanol (3A4O) was synthesized by the reduction of the 3-nitro-4-octanol by a Parr Autoclave unit. The stainless steel, 2 liter autoclave was loaded with Grace 3201 Raney Nickel (RaNi, 90 g wet, 45 g dry, 10 wt %) and methanol (MeOH, 300 g). The autoclave was sealed, assembled, purged with nitrogen then hydrogen, pressurized with hydrogen (600 psig), stirred at 600 RPM, and warmed to 40° C. The nitro-alcohol (491 g) was diluted with absolute ethanol (EtOH, 150 g) and pumped into the autoclave (4 ml/min) After 3.5 h the addition was complete and after 4 h the reaction was judged complete as no hydrogen uptake was observed. The autoclave was cooled, stirring stopped, vented, and purged with nitrogen. The autoclave was disassembled and the contents were vacuum filtered to remove the RaNi catalyst. This resulted in the isolation of a light yellow liquid (92 area %) that was concentrated in vacuo (55° C./full vacuum) before product was taken overhead (57-62° C./full vacuum). This resulted in the isolation of a clear, colorless, semi-solid (344 g, 95.3 area %, 75% overall yield) that contained some oxazolidine (2.2 area %) and some secondary amines (0.5 area %).

This compound was formulated at 8% by weight into a generic semi-synthetic metalworking fluid concentrate as described in Table 1. Identical formulations were prepared except substituting conventional amino alcohol compounds for 3A4O. The conventional amino alcohols were 2-amino-2-methyl-1-propanol (AMP) and n-butylethanolamine (BEA). An identical set of fluid concentrates was prepared including 1.5% of a 77% aqueous solution of 1,3,5-tris(2-hydroxyethyl)-s-triazine preservative, allowing us to evaluate fluids with and without preservative. The fluid concentrates were diluted at a rate of 20 parts Chicago tap water to 1 part fluid concentrate (by weight); the active amino alcohol concentration at dilution was therefore approximately 0.4% and the active preservative dosage (in the preserved set) was approximately 0.058%. These fluids were subjected to microbial challenge testing by ASTM Practice E 2275-03. In this method fluids are inoculated initially and then weekly with a mixed bacterial/fungal inoculum isolated from spoiled metalworking fluids. The bacterial and fungal counts are measured weekly using a serial dilution plate count method, and reported as colony forming units per milliliter (CFU/mL). The lower the CFU/mL the better the microbial control, and the longer the predicted service life of the fluid. The microbial results are described in FIGS. 1 & 2 (unpreserved) and FIGS. 3 & 4 (preserved with triazine). The unpreserved fluids exhibit the expected behavior, with a slight drop in initial counts due to microbial acclimation followed by rapid growth. The preserved fluids show the expected drop in counts initially, however the fluid with 3A4O shows an unexpected reduction in growth rate over the full course of the test. This is especially significant in the case of fungi, because triazine preservative is not effective against fungi at the dosage used.

TABLE 1

Semi-Synthetic Metalworking Fluid Concentrate

| INGREDIENT | MANUFACTURER | AMP | 3A4O | BEA |
|---|---|---|---|---|
| Hydrocal 100 Oil (severely hydrotreated naphthenic oil) | Calumet Industries | 10.0 | 10.0 | 10.0 |
| Actrabase PS-470 (medium molecular weight sodium petroleum sulfonate) | Georgia-Pacific Corp. | 14.0 | 14.0 | 14.0 |
| ALKATERGE T-IV (ethoxylated oleyl oxazoline) | ANGUS Chemical Co. | 4.0 | 4.0 | 4.0 |
| Xtol 304 (tall oil fatty acid) | Georgia-Pacific Corp. | 8.0 | 8.0 | 8.0 |
| Actrafos 110 (phosphate ester) | Georgia-Pacific Corp. | 2.4 | 2.4 | 2.4 |
| Dowanol PnB (propylene glycol n-butylether) | The Dow Chemical Co. | 6.0 | 6.0 | 6.0 |
| Amino Alcohol | See previous section | 8.0 | 8.0 | 8.0 |
| Potassium Hydroxide 50% (aqueous) | — | 1.0 | 3.6 | 1.2 |
| Igepal CO-630 (ethoxylated nonyl phenol) | Rhodia Corp. | 6.4 | 6.4 | 6.4 |
| Corfree M1 (C10 to C12 dibasic acid mixture) | Invista Corp. | 4.2 | 4.2 | 4.2 |
| Deionized Water | — | 36.0 | 33.4 | 35.8 |
| TOTAL | | 100 | 100 | 100 |

Example B

Preparation and Evaluation of 2-Amino-3-Heptanol Alkanolamine

Preparation of the 2-nitro-3-heptanol from nitroethane (NE) and valeraldehyde. In a similar fashion as before, a sample of 2-nitro-3-heptanol was synthesized by the addition of nitroethane (NE, 275 g, 3.67 mols) into a 1 liter 3-necked round-bottomed flask (RBF, 24/40, 29/42, 24/40) equipped with a thermocouple, a magnetic stirrer, a 500 ml addition funnel, a nitrogen inlet, and a glass stopper. The clear, colorless liquid was diluted by the addition of 95% ethanol (EtOH, 160 g) that resulted in an endotherm. The caustic catalyst was added (10 g of a 10% aqueous solution, 0.68 mole %) changing the reaction color to yellow and resulted in a slight exotherm. The valeraldehyde (258 g, 3.00 mols, 0.89 equivalents) was charged to the addition funnel and slowly added to the NE over 4 h. The heat of reaction raised the temperature to 40-45° C. Once the valeraldehyde addition was complete, the contents of the RBF were transferred into a 1 liter glass bottle, purged with nitrogen, and stored at ambient temperature at night and 50° C. during the day. The reaction progress was monitored by gas chromatography. After 6 days the conversion reached 81 area % and the reaction was stopped by the addition of a 10% aqueous hydrochloric acid solution (9 ml). The resulting pH=1 solution was concentrated in vacuo (50° C./full vacuum/0.5 h) to remove solvent and residual reagents. The resulting green solution (494 g, 90 area % corrected purity, 83% yield) was filtered (0.5 micron), purged with nitrogen, and stored in the refrigerator until needed.

Catalytic hydrogenation of the 2-nitro-3-heptanol to the 2-amino-3-heptanol alkanolamine. A sample of 2-amino-3-heptanol (2A3H) was synthesized by the reduction of the 2-nitro-3-heptanol by a Parr Autoclave unit. The stainless steel, 2 liter autoclave was loaded with Grace 3201 Raney Nickel (RaNi, 90 g wet, 45 g dry, 9 wt %) and methanol (MeOH, 300 g). The autoclave was sealed, assembled, purged with nitrogen then hydrogen, pressurized with hydrogen (600 psig), stirred at 600 RPM, and warmed to 40° C. The nitroalcohol (491 g) was diluted with absolute ethanol (EtOH, 150 g) and pumped into the autoclave (4 ml/min) After 3 h the addition was complete and after 3.5 h the reaction was judged complete as no hydrogen uptake was observed. The autoclave was cooled, stirring stopped, vented, and purged with nitrogen. The autoclave was disassembled and the contents were vacuumed filtered to remove the RaNi catalyst. This resulted in the isolation of a yellow liquid (82 area %) that was concentrated in vacuo (55° C./full vacuum) before product was taken overhead (40-50° C./full vacuum). This resulted in the isolation of a clear, colorless, solid (302 g, 91.2 area %, 64% overall yield) that contained some oxazolidine (3.4 area %).

This material was formulated into the same metalworking fluid concentrate described in Example A, at an 8% concentration. Identical fluids were prepared using 8% 2-amino-2-methyl-1-propanol (AMP) and 8% dicyclohexylamine (DCHA). The preservative benzisothiazolinone (BIOBAN BIT 20 DPG from Dow Biocides) was added to each fluid concentrate at 1.2%, giving an active concentration of 0.24% in the fluid concentrates and 0.012% in the use diluted fluids.

The diluted fluids were subjected to the same microbial testing protocol described in Example A, and the results are described in FIGS. 5 & 6. BIT is known not to be effective against pseudomonas aeroginosa, a typical gram negative bacterium found in metalworking fluids. This is apparent from the relatively poor performance against bacteria in the formulation with AMP. However, it was expected that DCHA which is known to enhance fluid life would have improved performance relative to AMP; this is not the case, in fact the opposite is true. It is also unexpected that the fluid with 2A3H should be more resistant to bacterial attack than the others, however a significant advantage is observed especially at the 4-8 week period. With respect to fungi, the fluid with 2A3H resists attack better than that with AMP, and is comparable in resistance to the fluid with DCHA. The results with 2A3H are unexpected because similar tests in unpreserved fluids show that it does not significantly inhibit bacterial or fungal growth.

Example C

Preparation and Evaluation of 2-amino-2-methyl-3-heptanol

Preparation of the 2-methyl-2-nitro-3-heptanol from 2-nitropropane (2-NP) and valeraldehyde. In a similar fashion as before, a sample of 2-methyl-2-nitro-3-heptanol was synthesized by the addition of 2-nitropropane (2-NP, 300 g, 3.37 mols) into a 1 liter 3-necked round-bottomed flask (RBF, 24/40, 29/42, 24/40) equipped with a thermocouple, a magnetic stirrer, a 500 ml addition funnel, a nitrogen inlet, and a glass stopper. The clear, colorless liquid was diluted by the addition of absolute ethanol (EtOH, 150 g) that resulted in an endotherm. The caustic catalyst was added (16 g of a 10% aqueous solution and 0.6 g of a 50% aqueous solution, 1.4 mole %) changing the reaction color to light yellow and resulted in a slight exotherm. The valeraldehyde (258 g, 3.00 mols, 0.89 equivalents) was charged to the addition funnel and slowly added to the 2-NP over 3 h. The heat of reaction raised the temperature to 40-45° C. Once the valeraldehyde addition was complete, the contents of the RBF were transferred into a 1 liter glass bottle, purged with nitrogen, and stored at ambient temperature. The reaction progress was monitored by gas chromatography and reached 72% completion after 3 weeks and the reaction was stopped by the addition of a 10% aqueous hydrochloric acid solution (16 ml). The resulting royal blue, pH=1 solution was concentrated in vacuo (50° C./full vacuum/0.5 h) to remove solvent and residual reagents. The resulting green solution (422 g, 90 area % corrected purity, 80% yield) was diluted with absolute ethanol (150 g), filtered (0.5 micron), purged with nitrogen, and stored in the refrigerator until needed.

Catalytic hydrogenation of the 2-methyl-2-nitro-3-heptanol to the 2-amino-2-methyl-3-heptanol. A sample of 2-amino-2-methyl-3-heptanol (2A2M3H) was synthesized by the reduction of the 2-methyl-2-nitro-3-heptanol by a Parr Autoclave unit. The stainless steel, 2 liter autoclave was loaded with Grace 3201 Raney Nickel (RaNi, 90 g wet, 45 g dry, 10 wt %) and methanol (MeOH, 300 g). The autoclave was sealed, assembled, purged with nitrogen then hydrogen, pressurized with hydrogen, stirred at 600 RPM, and warmed to 40° C. The yellow nitro-alcohol (422 g) had been diluted with absolute ethanol (EtOH, 150 g) and was pumped into the autoclave (4 ml/min) After 3 h the addition was complete and after 3.5 h the reaction was judged complete as no hydrogen uptake was observed. The autoclave was cooled, stirring stopped, vented, and purged with nitrogen. The autoclave was disassembled and the contents were vacuum filtered to remove the RaNi catalyst. This resulted in the isolation of a light yellow liquid (80 area %) that was concentrated in vacuo (55° C./full vacuum) before product was taken overhead (50-52° C./full vacuum). This resulted in the isolation of a clear, colorless, solid (268 g, 91.9 area %, 57% overall yield) that contained some oxazolidine (4.9 area %).

This material was formulated into the semi-synthetic metalworking fluid concentrate described previously, at a level of 8%. The triazine preservative described previously (77% active) was added at a level of 1.5%. Identical fluids were prepared using AMP, 3A4O and 2A3H. These fluids were then subjected to the same ASTM microbial challenge test described in the previous examples, except that the fluids were inoculated using a standard ATTCC strain (700505) of mycobacterium immunogenum. This can be a difficult microorganism to control because of its lipophilic cell wall structure, and has been implicated recently in outbreaks of an illness commonly known as hypersensitivity pneumonitis (HP). The data showing resistance of the above fluids toward this organism are found in FIG. 7. The control fluid with AMP gives the expected response with virtually no inhibition of activity. The other fluids, however, show unexpected resistance to this organism.

Example D

Investigation of Use Levels

In order to understand the influence of use level of the amino alcohols of the invention, we prepared similar semi-synthetic fluid concentrates as described previously but using 4% amino alcohol to give 2000 ppm at use dilution; the difference in the formulation was made up with water. The fluid concentrates were preserved with the same level of triazine-77% described previously. These fluids were diluted and subjected to the same bacterial/fungal challenge tests described in Examples A and B; the data are found in FIGS. 8 & 9. Fluids containing the amino alcohols of the invention exhibit significantly better resistance to both bacteria and fungi than the fluid containing the conventional amino alcohol AMP.

Example E

Preparation of 2-amino-4-ethyl-3-octanol

Preparation of the 2-nitro-4-ethyl-3-octanol from nitroethane and 2-ethylhexanal. In a similar fashion as before, a sample of 2-nitro-4-ethyl-3-octanol was synthesized by the addition of nitroethane (NE, 200 g, 2.67 mols) into a 1 liter 3-necked round-bottomed flask (RBF, 24/40, 29/42, 24/40) equipped with a thermocouple, a magnetic stirrer, a 500 ml addition funnel, a nitrogen inlet, and a glass stopper. This was diluted by the addition of absolute ethanol (EtOH, 150 g) that resulted in an endotherm. Deionized water (7.5 g) followed by the caustic catalyst (8.0 ml of a 10% aqueous solution) was added. The reaction color darkened to orange and a slight exotherm was observed. The 2-ethylhexanal (307 g, 2.40 mols, 0.90 equivalents) was charged to the addition funnel and slowly added to the NE over 3.5 h. The heat of reaction raised the temperature to 30° C. Once the valeraldehyde addition was complete, the contents of the RBF were transferred into a 1 liter glass bottle, purged with nitrogen, and stored at ambient temperature. The reaction progress was monitored by gas chromatography. After 2 days the measured conversion was 53.2 area % and 55.8 area % after 2 weeks. The reaction was then stopped by the addition of a 10% aqueous hydrochloric acid solution (8 ml) and the pH=1 solution was concentrated in vacuo (55° C./full vacuum/0.5 h) to remove solvent and residual reagents. The resulting yellow solution (362 g, 72 area % purity, 74.3% yield) was filtered (0.5 micron), purged with nitrogen, and stored in the refrigerator until needed.

Catalytic hydrogenation of the 2-nitro-4-ethyl-3-octanol to the 2-amino-4-ethyl-3-octanol amino alcohol. A sample of 2-amino-4-ethyl-3-octanol was synthesized by the reduction of the 2-nitro-4-ethyl-3-octanol by a Parr Autoclave unit. The stainless steel, 2 liter autoclave was loaded with Grace 3201 Raney Nickel (RaNi, 70 g wet, 35 g dry, 10 wt %) and methanol (MeOH, 300 g). The autoclave was sealed, assembled, purged with nitrogen then hydrogen, pressurized with hydrogen (750 psig), stirred at 600 RPM, and warmed to 40° C. The nitro-alcohol (362 g) was diluted with methanol MeOH, 380 ml) and pumped into the autoclave (5 ml/min). After 2 h the addition was complete and after another 15 min the reaction was judged complete as no hydrogen uptake was observed. The autoclave was cooled, stirring stopped, vented, and purged with nitrogen. The autoclave was disassembled and the contents were vacuum filtered to remove the RaNi catalyst. This resulted in the isolation of a light yellow liquid (84 area % pure) that was concentrated in vacuo (55° C./full vacuum) before product was taken overhead (122° C./15 mm) using a vacuum jacketed 18" vigreux column/head assembly. This resulted in the isolation of product as a clear, colorless, solution (182 g, 96.9 area %, 44% overall yield).

Example F

Further Evaluation of 3-Amino-4-Octanol

FIGS. 10-17 provide additional comparisons between 3-amino-4-octanol (3A4O), an aminoalcohol of the invention, and the non-invention aminoalcohol compounds 2-amino-2-methyl-1-propanol (AMP) and n-butylethanolamine (BEA), in conjunction with various biocides. In particular, FIGS. 10 and 11 bacterial and fungal efficacy comparisons of the aminoalcohols with BIOBAN P-1487 (a combination of 4-(2-nitrobutyl)-morpholine with 4,4'-(2-ethyl-2-nitrotrimethylene)dimorpholine). This biocide was added to give 750 ppm in the diluted fluid. The amine dosage was adjusted to give 4000 ppm at dilution. FIGS. 12 and 13 show bacterial and fungal efficacies of the aminoalcohols in the presence of a triazine/IPBC biocide blend. Triazine-78% was added at 750 ppm based on diluted fluid and iodopropynylbutylcarbamate (IPBC) added at 300 ppm active at dilution. The amine dosage was adjusted to give 3000 ppm at dilution. FIGS. 14 and 15 show bacterial and fungal efficacy of the compounds with Benzisothiazolinone (BIT). BIT was added at 120 ppm active based on diluted fluid and iodopropynylbutylcarbamate (IPBC) added at 300 ppm active at dilution. The amine dosage was adjusted to give 3000 ppm at dilution. FIGS. 16 and 17 show bacterial and fungal efficacy of the aminoalcohols with a chloromethylisothiazolinone/methylisothiazolinone (CMIT/MIT) blend. The blend was added directly to the diluted fluid to give 12 ppm actives; the product used was BIOBAN CM14 supplied by Dow Biocides. The amine dosage was adjusted to give 3000 ppm at dilution The data generally show the increased enhancement of biocide efficacy with the 3A4O of the invention, as compared to the other aminoalcohols. In addition, even where enhancement of efficacy against bacteria between the 3A4O and the other aminoalcohols tested is similar, the 3A4O generally shows greater enhancement against fungi. Thus, the 3A4O provides broader based biocide enhancement, making the material much more desirable as a preservative enhancer.

The invention has been described with reference to various specific and preferred embodiments and techniques. However, it should be understood that many variations and modifications may be made while remaining within the spirit and scope of the invention.

What is claimed is:

1. A biocidal composition comprising:
   a biocidal agent selected from the group consisting of 1,3,5-tris(2-hydroxyethyl)-s-triazine, iodopropynylbutylcarbamate, 1,2-benzisothiazolin-3-one, 4,4-dimethyloxazolidine, 7-ethyl bicyclooxazolidine, a combination of 4-(2-nitrobutyl)-morpholine with 4,4'-(2-ethyl-2-nitrotrimethylene)dimorpholine, 2-methyl-4-isothiazolin-3-one, a combination of 5-chloro-2-methyl-4-isothiazolin-3-one with 2-methyl-4-isothiazolin-3-one, 2-bromo-2-nitro-1,3-propanediol, octylisothiazolinone, dichloro-octylisothiazolinone, dibromo-octylisothiazolinone, phenolics and their corresponding sodium and/or potassium salts, sodium pyrithione, zinc pyrithione, n-butyl benzisothiazolinone, 1-(3-chloroallyl)-3,5,7-triaza-1-azoniaadamantane chloride, chlorothalonil, carbendazim, diiodomethyltolylsulfone, trimethyl-1,3,5-triazine-1,3,5-triethanol, 2,2-dibromo-3-nitrilopropionamide, glutaraldehyde, N,N'-methylene-bis-morpholine, ethylenedioxy methanol, phenoxyethanol, tetramethylol acetylenediurea, dithiocarbamates, 2,6-dimethyl-m-dioxan-4-ol acetate, dimethylol-dimethylhydantoin, tris(hydroxymethyl)nitromethane, bicyclic oxazolidines, and mixtures of two or more thereof; and
   a primary amino alcohol compound of the formula:

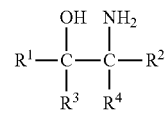

wherein
   $R^1$ and $R^3$ are each independently H, linear or branched alkyl, cycloalkyl, or $R^1$ is aryl while $R^3$ is H,
   $R^2$ and $R^4$ are each independently H or alkyl, provided that $R^2$ and $R^4$ together contain 2 or fewer carbon atoms;
   wherein alkyl, cycloalkyl, and aryl are optionally substituted with alkyl, and wherein the compound of formula (I) contains at least 6 carbon atoms,
   and wherein the biocidal agent and the primary amino alcohol are present in an effective amount to inhibit the growth of microorganisms in an aqueous-based system.

2. The composition of claim 1 wherein the primary amino alcohol compound comprises no more than 12 carbon atoms.

3. The composition of claim 1 further comprising one or more compounds selected from the group consisting of 2-amino-2-methyl-1-propanol, 2-amino-1-ethanol, 1-amino-2-propanol, bis(2-hydroxypropyl)amine, tris(2-hydroxypropyl)amine, bis(2-hydroxyethyl)amine, tris(2-hydroxyethyl)amine, and 2-(2-aminoethoxy)ethanol.

4. The composition of claim 1 wherein $R^2$ is methyl.

5. The composition of claim 1 wherein $R^2$ is ethyl.

6. The composition of claim 1 wherein the amino alcohol compound is of the formula (II):

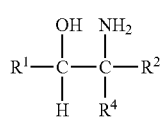

wherein
R¹ is $C_2$-$C_6$ alkyl; and
R² and R⁴ are each independently H or $C_1$-$C_2$ alkyl, wherein R² and R⁴ together contain 2 or fewer carbon atoms, and wherein the compound of formula (II) contains at least 6 carbon atoms.

7. The composition of claim 1 wherein the amino alcohol compound is selected from the group consisting of: 2-amino-3-hexanol, 2-amino-2-methyl-3-hexanol, 3-amino-4-octanol, 2-amino-2-methyl-3-heptanol, 2-amino-4-ethyl-3-octanol, 2-amino-3-heptanol, 2-amino-1-phenylbutanol, and mixtures thereof.

8. The composition of claim 1 wherein the amino alcohol is 3-amino-4-octanol.

9. A method of inhibiting the growth of microorganisms in an aqueous-based system comprising adding to said system an effective amount of a biocidal composition according to claim 1.

10. A method according to claim 9 wherein the aqueous-based system is a metal working fluid.

11. A metalworking fluid concentrate comprising a biocidal composition according to claim 1.

12. A metalworking fluid comprising a biocidal composition according to claim 1.

13. A metalworking fluid comprising water and a metalworking concentrate, wherein the metalworking concentrate comprises a biocidal composition according to claim 1.

14. A composition in which microbial growth is inhibited comprising: an aqueous based system; and a biocidal composition according to claim 1.

15. The composition according to claim 14 wherein the aqueous based system is latexes, water-based paints, water-based coatings, caulks, adhesives, tape joint compounds, mineral slurries, water-cooling systems, personal care products, soaps and detergents, disinfectants, cleaners, sanitizers, pesticide products, oilfield water, and water-based fluids used in oilfield applications such as drilling muds, fracturing fluids, and hydrotest fluids.

16. The composition according to claim 14 wherein the aqueous based system is a metal working fluid.

17. A compound selected from the group consisting of 2-amino-4-ethyl-3-octanol, 2-amino-2-methyl-3-heptanol, and salts thereof.

18. The composition of claim 1 wherein the biocidal agent is a triazine compound, a phenolic compound, iodopropynylbutylcarbamate, a combination of 4-(2-nitrobutyl)-morpholine with 4,4'-(2-ethyl-2-nitrotrimethylene)dimorpholine, 1,2-benzisothiazolin-3-one, 2-methyl-4-isothiazolin-3-one, a combination of 5-chloro-2-methyl-4-isothiazolin-3-one with 2-methyl-4-isothiazolin-3-one, octylisothiazolinone, dichloro-octylisothiazolinone, dibromo-octylisothiazolinone, n-butyl benzisothiazolinone, n,n'-methylene-bis-morpholine, or a mixture thereof.

* * * * *